United States Patent
Kim et al.

(10) Patent No.: US 12,385,180 B2
(45) Date of Patent: Aug. 12, 2025

(54) CLOTHING MANAGEMENT DEVICE AND CONTROL METHOD THEREFOR

(71) Applicant: Samsung Electronics Co., Ltd., Suwon-si (KR)

(72) Inventors: Seonghwan Kim, Suwon-si (KR); Jangpyo Park, Suwon-si (KR); Sanghun Lee, Suwon-si (KR); Yongwon Jeong, Suwon-si (KR); Joonho Kim, Suwon-si (KR); Hyoungkyun Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 203 days.

(21) Appl. No.: 17/738,509

(22) Filed: May 6, 2022

(65) Prior Publication Data
US 2022/0259794 A1 Aug. 18, 2022

Related U.S. Application Data

(63) Continuation of application No. PCT/KR2020/001266, filed on Jan. 28, 2020.

(30) Foreign Application Priority Data

Dec. 17, 2019 (KR) ........................ 10-2019-0169207

(51) Int. Cl.
*D06F 58/20* (2006.01)
*D06F 34/18* (2020.01)
(Continued)

(52) U.S. Cl.
CPC ............ *D06F 58/203* (2013.01); *D06F 34/18* (2020.02); *D06F 58/10* (2013.01);
(Continued)

(58) Field of Classification Search
CPC ........................................................ F24F 8/50
See application file for complete search history.

(56) References Cited

U.S. PATENT DOCUMENTS 7,610,779 B2    11/2009  Yang et al.
9,322,124 B1 *  4/2016   Al-Hasan ............... D06F 58/203
(Continued)

FOREIGN PATENT DOCUMENTS

CN    204444820 U    7/2015
CN    204838579 U    12/2015
(Continued)

OTHER PUBLICATIONS

Korean Office Action dated Mar. 27, 2025, issued in Korean Application No. 10-2019-0169207.

*Primary Examiner* — Omair Chaudhri
(74) *Attorney, Agent, or Firm* — Jefferson IP Law, LLP

(57) ABSTRACT

An electronic device and a control method therefor are provided. The clothing management device includes a sensor, a deodorizing device for removing a contaminant source of clothing received in the clothing management device, a perfuming device for spraying aroma onto clothing, and a processor for, when a user command for managing clothing is received, controlling the deodorizing device to perform deodorization for removing a contaminant source of the clothing, and, when it is determined that the concentration of the contaminant source in the clothing management device sensed by the sensor is less than or equal to a preconfigured threshold value, controlling the deodorizing device to stop the deodorization and controlling the perfuming device to perfume the clothing by using aroma.

15 Claims, 16 Drawing Sheets

(51) Int. Cl.
  *D06F 58/10* (2006.01)
  *D06F 103/02* (2020.01)
  *D06F 103/36* (2020.01)
  *D06F 105/40* (2020.01)
  *D06F 103/56* (2020.01)

(52) U.S. Cl.
  CPC ...... *D06F 2103/02* (2020.02); *D06F 2103/36* (2020.02); *D06F 2103/56* (2020.02); *D06F 2105/40* (2020.02)

(56) References Cited

U.S. PATENT DOCUMENTS

| | | | |
|---|---|---|---|
| 9,988,756 B2 | 6/2018 | Bae et al. | |
| 10,119,221 B2 | 11/2018 | Nam et al. | |
| 2004/0134094 A1* | 7/2004 | Hahn | D06F 58/203 34/595 |
| 2005/0016012 A1* | 1/2005 | Yang | D06F 73/02 34/486 |
| 2005/0262883 A1* | 12/2005 | Yang | D06F 33/65 68/17 R |
| 2008/0052950 A1* | 3/2008 | Park | D06F 39/125 34/524 |
| 2008/0193328 A1* | 8/2008 | Crapser | A61L 9/22 422/5 |
| 2010/0077628 A1* | 4/2010 | Bae | D06F 58/203 34/130 |
| 2010/0101280 A1* | 4/2010 | Im | D06F 39/40 68/19 |
| 2010/0132209 A1* | 6/2010 | Park | D06F 58/203 34/201 |
| 2010/0139366 A1* | 6/2010 | Krausch | D06F 34/14 68/13 R |
| 2010/0281924 A1* | 11/2010 | Tobi | D06F 25/00 68/19 |
| 2011/0308102 A1* | 12/2011 | Bae | D06F 58/30 34/329 |
| 2012/0160269 A1* | 6/2012 | Pyo | D06F 58/44 134/25.1 |
| 2014/0059881 A1* | 3/2014 | Kim | D06F 29/005 34/493 |
| 2016/0177497 A1* | 6/2016 | Choi | F01K 5/00 68/5 C |
| 2016/0289887 A1* | 10/2016 | Al-Harthi | D06F 63/00 |
| 2017/0145623 A1* | 5/2017 | Jung | D06F 58/203 |
| 2018/0038041 A1* | 2/2018 | Longinotti-Buitoni | D06F 35/001 |
| 2018/0155865 A1* | 6/2018 | Nagai | A61L 9/122 |
| 2018/0320303 A1* | 11/2018 | Valzelli | D06F 58/10 |
| 2019/0301078 A1* | 10/2019 | Leibman | D06F 58/203 |
| 2020/0069146 A1* | 3/2020 | Kessler | D06F 58/203 |
| 2020/0131687 A1* | 4/2020 | Wright | D06F 39/022 |
| 2020/0248352 A1* | 8/2020 | Cooke | D06F 33/32 |
| 2020/0283699 A1* | 9/2020 | Cooke | C11D 17/041 |
| 2021/0040675 A1 | 2/2021 | Park et al. | |
| 2021/0115612 A1* | 4/2021 | Han | D06F 34/14 |
| 2022/0042231 A1* | 2/2022 | Jang | G06Q 30/0631 |

FOREIGN PATENT DOCUMENTS

| | | | | |
|---|---|---|---|---|
| EP | 2420610 B1 * | 2/2017 | ............ | D06F 39/005 |
| KR | 10-2001-0036313 A | 5/2001 | | |
| KR | 10-0765278 B1 | 10/2007 | | |
| KR | 10-2010-0023322 A | 3/2010 | | |
| KR | 10-1022217 B1 | 3/2011 | | |
| KR | 10-1040386 B1 | 6/2011 | | |
| KR | 10-2014-0016093 A | 2/2014 | | |
| KR | 10-1521917 B1 | 5/2015 | | |
| KR | 10-1521918 B1 | 5/2015 | | |
| KR | 10-2016-0044886 A | 4/2016 | | |
| KR | 10-1685346 B1 | 12/2016 | | |
| KR | 10-1867393 B1 | 6/2018 | | |
| KR | 20180097326 A * | 8/2018 | | |
| KR | 10-2019-0089563 A | 7/2019 | | |
| WO | WO-2016074604 A1 * | 5/2016 | ............. | D06F 57/00 |
| WO | WO-2017004787 A1 * | 1/2017 | ............. | D06F 33/02 |
| WO | WO-2018177108 A1 * | 10/2018 | ........... | D06F 58/203 |

* cited by examiner

FIG. 12

| SUBSTANCE NAME | CHEMICAL FORMULA /MOLECULAR FORMULA | ODOR CHARACTERISTIC | ODOR THRESHOLD (ppb) | BOILING POINT (°C, 760mmHg) | MOLAR MASS (g/mol) |
|---|---|---|---|---|---|
| PYRIDINE | $C_6H_5N$ | CIGARETTE ODOR | 3.7 | 115 | 79.1 |
| VALERALDEHYDE | $C_6HO$ | PORK BELLY MEAT ODOR | - | 104 | 86.13 |
| ISOVALERIC ACID | $C_5H_{10}O_2$ | PERSPIRATION ODOR | - | 176.5 | 102.13 |
| ACETALDEHYDE | $CH_3CHO$ | STRONG FRUIT SCENT | 4 | 20.2 | 44.05 |
| ALLYL MERCAPTAN | $C_3H_6S$ | STRONG GARLIC SCENT, COFFEE SCENT | 0.05 | 67 | 74.2 |
| AMMONIA | $NH_3$ | PUNGENT ODOR | 37 | -33.34 | 17.031 |
| BUTYLAMINE | $C_4H_{11}N$ | SPOILED ODOR OR AMMONIA ODOR | - | 78 | 73.14 |
| DIBUTYLAMINE | $C_8H_{19}N$ | FISHY ODOR | 16 | 159 | 129.24 |
| DIISOPROPYLAMINE | $C_6H_5N$ | FISHY ODOR | 3.5 | 84 | 101.19 |
| DIMETHYLAMINE | $(CH_3)_2NH$ | FISHY ODOR | 47 | 7 | 45.08 |
| DIMETHYL SULFIDE | $C_2H_6S$ | ROTTEN CABBAGE ODOR | 1 | 37.34 | 62.1 |
| ETHYLAMINE | $C_2H_5NH_2$ | STRONG AMMONIA ODOR | 830 | 16.6 | 45.08 |
| ETHANETHIOL | $C_2H_6S$ | ROTTEN CABBAGE ODOR | 0.19 | 35 | 62.13 |
| HYDROGEN SULFIDE | $H_2S$ | ROTTEN EGG ODOR | 0.47 | -60 | 34.1 |
| METHYLAMINE | $CH_3NH_2$ | FISHY ODOR | 21 | -6 | 31.05 |
| METHANETHIOL | $CH_4S$ | ROTTEN CABBAGE ODOR | 1.1 | 5.95 | 48.1 |
| SULFUR DIOXIDE | $SO_2$ | STRONG PUNGENT ODOR | 9 | -10 | 64.1 |

CLOTHING MANAGEMENT DEVICE AND CONTROL METHOD THEREFOR

CROSS-REFERENCE TO RELATED APPLICATION(S)

This application is a continuation application, claiming priority under § 365(c), of an International application No. PCT/KR2020/001266, filed on Jan. 28, 2020, which is based on and claims the benefit of a Korean patent application number 10-2019-0169207, filed on Dec. 17, 2019, in the Korean Intellectual Property Office, the disclosure of which is incorporated by reference herein in its entirety.

BACKGROUND

1. Field

The disclosure relates to a clothing management device and a control method therefor. More particularly, the disclosure relates to a clothing management device which manages clothing using a gas sensor and a control method therefor.

2. Description of Related Art

Recently, as a separate electronic device from a washer which requires washing water, clothing management devices having functions such as removing wrinkles on clothing through a method of spraying air such as steam, or removing dust or odor on clothing, and the like are being developed. The clothing management device may process or manage clothing more conveniently.

Here, with respect to the removal of an odor on clothing, the clothing management device may uniformly remove a substance (hereinbelow, a contaminant source) giving off an odor (e.g., malodor) from the clothing by performing a pre-set deodorizing operation for a pre-set time in a deodorizing function based on the deodorizing function (or a clothing management course including the deodorizing function) being selected by a user.

In this case, there may be the problem of efficiency deteriorating such as the contaminant source remaining even if the deodorizing operation of the clothing management device has been completed or the clothing management device continuing to perform the deodorizing operation even if the contaminant source is fully removed. This is because the difference in the deodorizing extent (or an extent of the contaminant source being removed) generated according to a contamination degree of the clothing, a number of clothing, a type of clothing, and the like is not considered.

The clothing management device may also perform a function to coat the clothing with a fragrance in addition to the function of removing the odor of clothing. For example, the clothing management device may spray, after performing the deodorizing operation, a substance (hereinafter, an aroma) which gives off a fragrance on clothing on the clothing.

Here, even when the contaminant source is left remaining on the clothing by a certain level or more (when the contaminant source is not sufficiently removed), an instance of the aroma being sprayed on the clothing may occur. In this case, the odor (malodor) of the contaminant source and the odor (fragrance) of the aroma may be mixed and there may be the problem of an odor being generated which causes more displeasure to the user.

In addition to the above, there may be the problem of a concentration of the aroma released from the clothing being insufficient or excessive than the concentration desired by the user according to the number of clothing, the type of clothing, and the like in a state where the contaminant source is sufficiently removed.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a clothing management device which effectively removes an odor by using a sensor and a control method therefor.

Additional aspects will be set forth in part in the description which follows and, in part, will be apparent from the description, or may be learned by practice of the presented embodiments.

In accordance with an aspect of the disclosure, a clothing management device is provided. The clothing management device includes a sensor, a deodorizing device configured to remove a contaminant source of clothing which is contained in the clothing management device, a perfuming device configured to spray an aroma on the clothing, and a processor configured to control, based on a user command for managing the clothing being received, the deodorizing device to perform deodorization of removing the contaminant source of the clothing, and control, based on determining that a concentration of the contaminant source in the clothing management device which is detected by the sensor is less than or equal to a pre-set threshold value, the deodorizing device to stop the deodorization, and control the perfuming device to perform perfuming of the clothing by using the aroma.

The processor may be configured to perform, based on determining that the concentration of the contaminant source is less than or equal to the pre-set threshold value when the received user command is a command for performing the perfuming of the clothing, perfuming of the clothing, and control, based on the received user command being a command for not performing the perfuming of the clothing, the deodorizing device to proceed with the deodorization until the concentration of the contaminant source which is detected by the sensor reaches a target value which is lower than the pre-set threshold value.

The processor may be configured to control, based on determining that a target value has been reached according to a concentration of an aroma in the clothing management device which is detected by the sensor increasing, the perfuming device to stop the perfuming.

The deodorizing device may be configured to remove the contaminant source of the clothing by spraying steam toward the clothing, and the perfuming device may be configured to perform drying and perfuming of the clothing by using hot air after the deodorization is stopped.

The processor may be configured to control the perfuming device to supply the hot air into the clothing management device along a first flow path, and supply at least a portion of the hot air which moves along the first flow path into the clothing management device through a second flow path at which the aroma is disposed by adjusting a valve which is connected to the first flow path.

The processor may be configured to control the perfuming device to supply the hot air into the clothing management device along a plurality of flow paths, and the aroma may be disposed in at least one from among the plurality of flow paths.

The sensor may include a first gas sensor and a second gas sensor, and the processor may be configured to detect the concentration of the contaminant source through the first gas sensor which is disposed around a location at which the clothing is contained in the clothing management device, and detect the concentration of the aroma through the second gas sensor which is disposed around the location at which the aroma is sprayed from the perfuming device.

In accordance with another aspect of the disclosure, a control method of a clothing management device is provided. The control method includes performing, based on a user command for managing clothing being received, deodorization of removing a contaminant source of clothing which is contained in the clothing management device and stopping, based on determining that a concentration of a contaminant source in the clothing management device which is detected by the sensor is less than or equal to a pre-set threshold value, the deodorization and performing perfuming of the clothing by using an aroma.

The performing the perfuming may include performing, based on determining that the concentration of the contaminant source is less than or equal to the pre-set threshold value when the received user command is a command for performing the perfuming of the clothing, perfuming of the clothing, and performing, based on the received user command being a command for not performing the perfuming of the clothing, the deodorization until the concentration of the contaminant source which is detected by the sensor reaches a target value which is lower than the pre-set threshold value.

The method may further include stopping the perfuming based on determining that a target value has been reached according to a concentration of an aroma in the clothing management device which is detected by the sensor increasing.

The performing the deodorization may include removing a contaminant source of the clothing by spraying steam toward the clothing, and the performing the perfuming may include performing drying and perfuming of the clothing by using hot air after the deodorization is stopped.

The performing the perfuming may include supplying the hot air into the clothing management device along a first flow path and supplying at least a portion of the hot air which moves along the first flow path into the clothing management device through a second flow path at which the aroma is disposed by adjusting a valve which is connected to the first flow path.

The performing the perfuming may include supplying the hot air into the clothing management device along the plurality of flow paths, and the aroma may be disposed in at least one from among the plurality of flow paths.

The sensor may include a first gas sensor and a second gas sensor, and the method may further include detecting the concentration of the contaminant source through the first gas sensor which is disposed around a location at which the clothing is contained in the clothing management device and detecting the concentration of the aroma through the second gas sensor which is disposed around a location at which the aroma is sprayed.

According to the various embodiments as described above, a clothing management device which effectively removes an odor by using a sensor and a control method therefor may be provided.

In addition, according to an embodiment, an optimized deodorizing operation may be performed by detecting a substance causing the odor from the clothing in real-time, and may reduce a deodorizing operation time and enhance a power reduction effect and a deodorizing effect.

In addition, according to an embodiment, a concentration of an aroma fragrance which is to be coated on the clothing may be adjusted to a level desired by a user.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 12 is a diagram illustrating a contaminant source according to an embodiment of the disclosure.

Throughout the drawings, it should be noted that like reference numbers are used to depict the same or similar elements, features, and structures.

DETAILED DESCRIPTION

Figure 1:
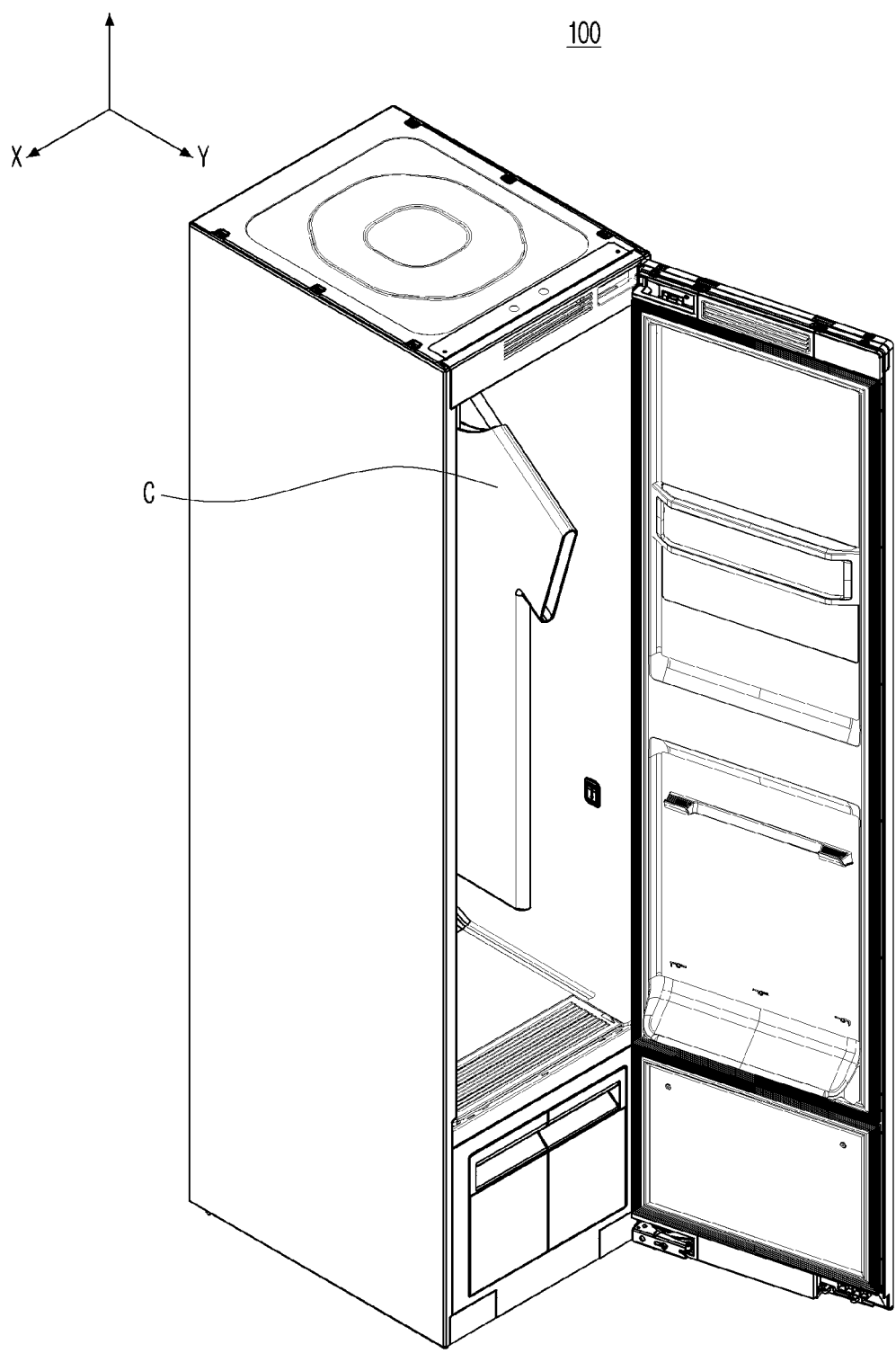
FIG. 1 is a diagram illustrating a clothing management device according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not for limited the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Expressions such as "first," "second," "1st," "2nd" or so on used herein may be used to refer to various elements regardless of order and/or importance, and it should be noted that the expressions are merely used to distinguish an element from another element and not to limit the relevant elements.

In the disclosure, expressions such as "A or B," "at least one of A and/or B," or "one or more of A and/or B" may include all possible combinations of the items listed together. For example, "A or B," "at least one of A and B," or "at least one of A or B" may refer to all cases including (1) at least one A, (2) at least one B, or (3) both of at least one A and at least one B.

It is to be understood that the terms such as "comprise" or "include" are used herein to designate a presence of a characteristic, number, step, operation, element, component, or a combination thereof, and not to preclude a presence or a possibility of adding one or more of other characteristics, numbers, steps, operations, elements, components or a combination thereof.

When a certain element (e.g., first element) is indicated as being "(operatively or communicatively) coupled with/to" or "connected to" another element (e.g., second element), it may be understood as the certain element being directly coupled with/to the another element or as being coupled through other element (e.g., third element). On the other hand, when a certain element (e.g., first element) is indicated as "directly coupled with/to" or "directly connected to" another element (e.g., second element), it may be understood as the other element (e.g., third element) not being present between the certain element and the another element.

The expression "configured to . . . (or set up to)" used in the disclosure may be used interchangeably with, for example, "suitable for . . . ," "having the capacity to . . . ," "designed to . . . ," "adapted to . . . ," "made to . . . ," or "capable of . . . " based on circumstance. The term "configured to . . . (or set up to)" may not necessarily mean "specifically designed to" in terms of hardware. Rather, in a certain circumstance, the expression "a device configured to . . . " may mean something that the device "may perform . . . " together with another device or components. For example, the phrase "a processor configured to (or set up to) perform A, B, or C" may mean a dedicated processor for performing the operation (e.g., embedded processor), or a generic-purpose processor (e.g., a central processing unit (CPU) or an application processor) capable of performing the operations by executing one or more software programs stored in the memory device.

FIG. 1 is a diagram illustrating a clothing management device according to an embodiment of the disclosure.

Referring to FIG. 1, a clothing management device 100 according to an embodiment may be implemented as an electronic device which removes odors, dust or wrinkles of clothing C (various items such as clothing, blankets, dolls and shoes are herein referred to as 'clothing') contained inside through a method of spraying air such as steam. For example, the clothing management device 100 according to the various embodiments may include at least one from among a clothing cleaning device, a clothing washing device, a clothing drying device, an air conditioner, an air cleaning device, a home automation control panel, a security control panel, an industrial or private robot, a point of sales (POS) of a store, or an internet of things, furniture or a part of a building/structure. According to various embodiments, the electronic device may be a combination of one or more from among the above-described various devices. The electronic device according to an embodiment is not limited to the above-described devices, and may include new electronic devices according to a development in technology.

The clothing management device 100 may perform deodorizing of removing an odor of a contaminant source of clothing C which is contained in the clothing management device. Here, the odor may generally refer to a property in which a volatilized (vaporized) volatile substance (or compound) is transferred to olfactory cells through a person's nose and sensed. In addition, the contaminant source may be various substances (or compounds) giving out an odor which presents displeasure or stimulate a typical user, or cause symptoms such as hyposmia, headaches, vomiting and motion sickness, and specifically, the contaminant source may include, for example, at least one from among the substances (or compounds) described in a table in FIG. 12. However, the contaminant source is not limited thereto, and the contaminant source may include a gaseous substance, a volatile compound, and the like which causes odor (malodor) giving displeasure and aversion by stimulating an olfactory sense of the typical user.

The clothing management device 100 may perform perfuming of the clothing C after performing deodorizing on the clothing C. Here, the perfuming may refer to coating the clothing C with a fragrance such as an aroma. The aroma may refer to various perfume substances giving off fragrances, and for example, the aroma may be various perfume substances or fresheners manufactured by being extracted from various parts of plants such as lavenders, eucalyptuses, roses, and oranges, or artificially synthesized.

According to an embodiment, the clothing management device 100 may detect a concentration of a contaminant source while performing deodorizing, stop deodorizing based on the concentration of the contaminant source, and perform the perfuming which uses an aroma. Further, the clothing management device 100 may detect the concentration of the aroma while performing perfuming, and stop perfuming based on the concentration of the aroma.

Here, the concentration of the contaminant source may be shown in various units such as mg/m3 or parts per million (ppm) according to an amount of the vaporized (volatilized) contaminant source present in an internal space (or specified location) of the clothing management device 100. Similarly, the concentration of the aroma may also be shown in various units such as mg/m3 or ppm according to the amount of the vaporized (volatilized) aroma present in the internal space (or specified location) of the clothing management device 100.

In an embodiment, the concentration of the contaminant source (or aroma) according to an embodiment may also be shown by substituting with an intensity (strength) of the odor with respect to the contaminant source (or aroma) as in Equation 1 below according to Weber-Fechner's law.

$$I = K * \log C \quad \text{Equation 1}$$

In Equation 1, I represents the intensity (strength) of the odor, K represents a constant which changes according to the type of the contaminant source (or aroma), and C represents the concentration of the contaminant source (or aroma). However, this is merely one embodiment, and the intensity of the odor with respect to the contaminant source (or aroma) may be modified with various equations.

According to an embodiment as described above, a clothing management device and a control method therefor in which the clothing management device 100 may effectively remove odors by using a gas sensor may be provided. In addition, according to an embodiment, an optimized deodorizing operation may be performed by detecting the substance causing the odor from the clothing C in real-time, and the deodorizing operation time may be reduced, and the power reduction effect and the deodorizing effect may be enhanced. In addition, according to an embodiment, the concentration of the aroma fragrance which is to be coated on the clothing C may be adjusted to an appropriate level.

The disclosure will be described in greater detail below with reference to the accompanied drawings.

Figure 2:
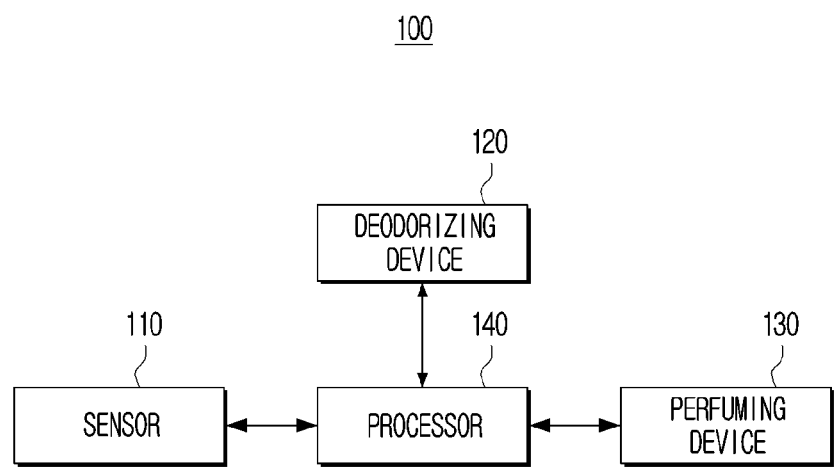
FIG. 2 is a block diagram illustrating a configuration of a clothing management device according to an embodiment of the disclosure.
Figure 3:
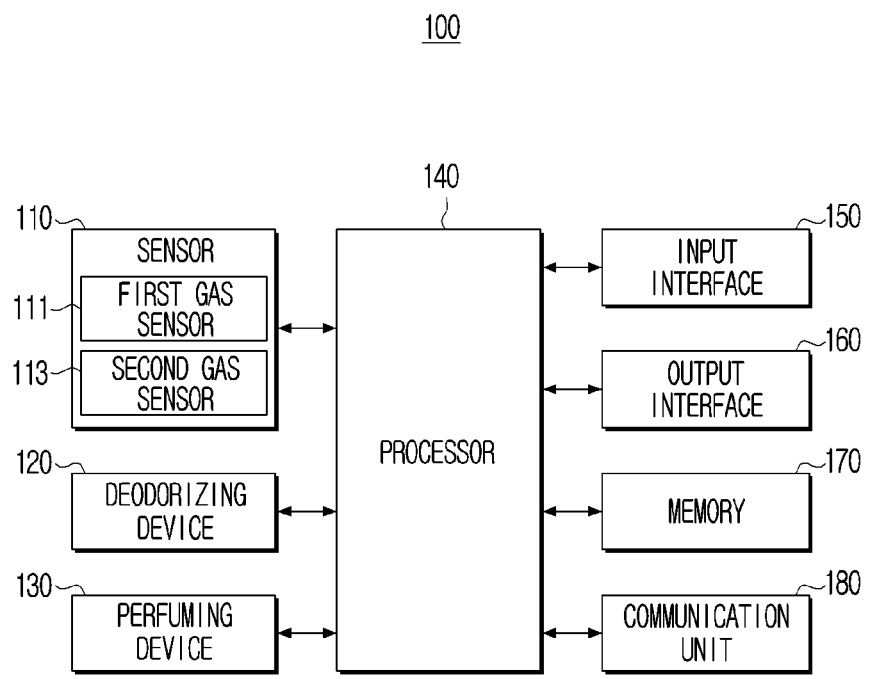
FIG. 3 is a block diagram illustrating an additional configuration of a clothing management device according to an embodiment of the disclosure.

FIG. 2 is a block diagram illustrating a configuration of a clothing management device according to an embodiment of the disclosure, and FIG. 3 is a block diagram illustrating an additional configuration of a clothing management device according to an embodiment of the disclosure.

Referring to FIG. 2, a clothing management device 100 may include a sensor 110, a deodorizing device 120, a perfuming device 130, and a processor 140.

The sensor 110 may be configured to detect the concentration of the contaminant source or aroma present inside of the clothing management device 100. For example, the sensor 110 may be configured to detect the amount of contaminant source (or aroma) in a gaseous state included inside of the clothing management device 100, or detect the amount of the contaminant source or aroma when the contaminant source (or aroma) in a liquid or solid state is vaporized (or evaporated) and dispersed in the air which is contained inside of the clothing management device 100. Alternatively, the sensor 110 may be configured to detect the intensity (or strength) of the odor with respect to the contaminant source (or aroma) present inside of the clothing management device 100.

To this end, the sensor 110 may be implemented as an electrochemical sensor, a semiconductor sensor, a photoionization sensor, or the like.

Here, the electrochemical sensor may be configured to detect the type, the concentration, the intensity, and the like of the contaminant source (or aroma) by measuring a change in electromotive force between an amount of electrons (current) or electrodes generated when the contaminant source (or aroma) produces an oxidation or reduction reaction by the workings of the embedded electrode according to various methods such as a galvanic cell method or a potentiostatic method. The semiconductor sensor may be configured to use various semiconductors such as $SnO_2$, $ZnO$, and $Fe_2O_3$, and detect the type, the concentration, the intensity, and the like of the contaminant source (or aroma) by measuring a change in electrical conductivity generated when the contaminant source (or aroma) contacts the semiconductor surface. The photoionization sensor may be configured to detect the type, the concentration, the intensity, and the like of the contaminant source (or aroma) by comparing a spectrum detected by an optical detector after light (e.g., infrared ray, etc.) from a light source or ultrasonic waves are irradiated with a characteristic of the contaminant source (or aroma) selectively absorbing light from a unique specific wavelength (absorption band) according to various methods such as a non-dispersive infrared (NDIR) method or a photo-acoustic method.

Referring to FIG. 3, a sensor 110 according to an embodiment may include a plurality of sensors. In an embodiment, the sensor 110 may include a first gas sensor 111 and a second gas sensor 113.

The first gas sensor 111 and the second gas sensor 113 may be disposed at different positions from each other. At this time, the first gas sensor 111 and the second gas sensor 113 may be implemented as sensors configured to measure the concentration of substances different from one another.

The first gas sensor 111 may be disposed around a position at which the clothing C is contained in the clothing management device 100 as a sensor for detecting the concentration of the contaminant source. For example, the first gas sensor 111 may be disposed within a pre-set radius based on a position of the clothing C or a position of a clothing support provided inside of the clothing management device 100. Here, the clothing support may function as where clothing C is to be laid.

The second gas sensor 113 may be disposed around the position at which the aroma is sprayed as a sensor for detecting the concentration of the aroma. For example, the second gas sensor 113 may be disposed within a pre-set radius based on the position at which the aroma is to be sprayed from the perfuming device 130 to the internal space of the clothing management device 100.

In this case, the processor 140 may be configured to detect the concentration of the contaminant source through the first gas sensor 111 disposed around the position at which the clothing C is contained in the clothing management device 100, and detect the concentration of the aroma through the second gas sensor 113 disposed around the position at which the aroma is to be sprayed from the perfuming device 130.

According to an embodiment as described above, even if a case in which the contaminant source and the aroma are mixed inside the clothing management device 100 or in a case in which a substance similar to the contaminant source and the aroma is included occurs, the first gas sensor 111 and the second gas sensor 113 may be configured to accurately classify and detect the concentrations of the contaminant source and the aroma from positions separated from each other.

The deodorizing device 120 may perform deodorizing of removing the contaminant source of the clothing C contained in the clothing management device 100. For example, the deodorizing device 120 may spray steam or air toward the clothing C contained in the internal space of the clothing management device 100 according to the control of the processor 140. At this time, the steam may refer to water ($H_2O$) particles which are in a gaseous state. Further, the steam may further include, not only water, but also various substances separate from what is to wash the contaminant source. In addition, the air may be compressed to a pressure higher than the atmosphere (hereinafter, high-pressure).

To this end, the deodorizing device 120 may include a water tank, a steam generator, and a discharging member. For example, the water tank may store water in the liquid state, and may be connected through a tube (or a pipe, a flow path, etc.) to supply water to the steam generator. The steam generator may convert the water into steam through heating (i.e., generate steam) when the water is supplied from the water tank. The steam generated through the heating device may be supplied to the discharging member which is connected through the tube (or a pipe, a flow path, etc.). The discharging member (e.g., a nozzle, etc.) may discharge steam toward the clothing C which is contained in the internal space of the clothing management device 100 when the steam is suppled from the steam generator.

In this case, the steam may remove the contaminant source present at a surface of a fabric or in a gap of a fabric forming the clothing C. For example, the steam contacts with the contaminant source and is condensed to a liquid state in which the contaminant source is dissolved, and the steam in the liquid state in which the contaminant source is dissolved may be collected through an outlet formed at a bottom surface inside of the clothing management device 100.

The deodorizing device 120 may include a compressor, and for example, the compressor may be a device configured to spray toward the clothing C through the discharging member (e.g., a nozzle, etc.) by compressing the air suctioned from the outside. The compressor may be configured to mechanically separate the contaminant source from the clothing C by spraying air (or high-pressure air) onto the clothing C. Further, it may also be possible for the deodorizing device 120 to spray steam together with high-pressure air toward the clothing C through the discharging member. In this case, the discharging member may be connected with the compressor and the steam generator.

The deodorizing device 120 may include a light source part and a photocatalyst.

The light source part may emit light (visible light, ultraviolet light, etc.) according to the control of the processor 140, and provide the emitted light as the photocatalyst. To this end, the light source part may be implemented as various devices such as light emitting diodes (LEDs) and a laser diode (LD) lamp.

The photocatalyst may be activated by the light provided from the light source part, and the photocatalyst may function as a catalyst while being activated and degrade the contaminant source to a substance which does not cause an odor such as carbon dioxide ($CO_2$) and water ($H_2O$). To this end, the photocatalyst may be implemented as various substances such as titanium dioxide ($TiO_2$), ZnO, $ZrO_2$, $WO_3$, and Perovskite-like mixed metal oxide.

The perfuming device 130 may be configured to perform the perfuming of spraying an aroma to the clothing C contained in the clothing management device 100. For example, the perfuming device 130 may be configured to spray an aroma toward the clothing C contained in the internal space of the clothing management device 100 according to the control of the processor 140. Here, the aroma may be disposed and stored on the flow path which connects the insides of the perfuming device 130 and the clothing management device 100, and the aroma may be required to be replaced according to the number of use or amount used as a consumable product.

Here, the perfuming device 130 may be implemented in various structures according to an aroma spraying form based on the state (solid or liquid, etc.).

In an embodiment, the perfuming device 130 may be implemented in a structure including a heater which generates hot air (high-temperature air) and an air circulation device. Here, the heater may generate hot air by heating air, and the heater may be implemented as a device of various methods such as a vent (hot air exhaust type drying) method, a condensing (hot air dehumidification) method, and a heat pump (low-temperature dehumidification) method. In addition, the air circulation device may include a fan, and may discharge air inside of the clothing management device 100 to the perfuming device through the fan, or supply air inside of the perfuming device to the inside of the clothing management device 100.

In this case, the perfuming device 130 may generate hot air through the heater, and when the hot air is supplied inside of the clothing management device 100 through the flow path at which the aroma in the solid state is disposed by the air circulation device, the aroma which is vaporized according to the flow of hot air may reach the clothing C. In addition, in this case, the perfuming device 130 may remove the moisture present in the clothing C and dry the clothing C by continuously circulating the high-temperature air inside of the clothing management device 100.

In addition, in an embodiment, the perfuming device 130 may be implemented as a structure including a steam generator which generates high-temperature steam and an air circulation device. In this case, the perfuming device 130 may generate high-temperature steam through the steam generator, and based on providing the high-temperature steam to the inside of the clothing management device 100 through the flow path at which the aroma in the solid state is disposed by the fan, the aroma dissolved by the steam may reach the clothing C.

In addition, in an embodiment, the perfuming device 130 may be implemented in a structure such as a spray. In this case, the perfuming device 130 may spray the aroma in the liquid state toward the clothing C. At this time, based on the perfuming device 130 spraying the aroma in the liquid state which is stored in a sealed container through the nozzle, the aroma in the liquid state in a mist like form may reach the clothing C. Here, the size of the aroma particle sprayed according to an internal (high-pressure) and an external (low-pressure) pressure difference in the container in which the aroma is sealed may vary.

In addition, in an embodiment, the perfuming device 130 may be implemented in a structure including an ultrasound generator which generates ultrasonic waves and a nozzle. For example, the perfuming device 130 may convert the aroma in liquid state to particles of a fine size by vibrating through ultrasonic waves, and spray the aroma particles in the liquid state to the clothing C through the nozzle.

The processor 140 may be configured to control the overall operation of the clothing management device 100. To this end, the processor 140 may be electrically connected to each configuration of the clothing management device 100. Specifically, the processor 140 may be configured to determine a sequence for processing data by reading and interpreting at least one instruction, and transfer a control signal controlling an operation of another configuration to another configuration. At this time, the at least one instruction may be stored in a memory (not shown) provided inside of the processor 140, or stored in a memory 170 (referring to FIG. 3) provided in an electronic device (e.g., the clothing management device 100). Accordingly, each configuration of the clothing management device 100 may operate according to the control of the processor 140.

The processor 140 may be configured with one or a plurality of processors, and the processor 140 may be implemented as a generic purpose processor such as a central processing unit (CPU) and an application processor (AP), a graphics dedicated processor such as a graphics processing unit (GPU) and a vision processing unit (VPU), an artificial intelligence dedicated processor such as a neural processing unit (NPU), or the like. Meanwhile, the GPU may be implemented as a separate device from the processor 140. In addition, the CPU and GPU may be configured to perform, in connection, an operation of the disclosure. At this time, the GPU may be implemented in a structure having several hundred or several thousand cores specializing in a parallel processing method which processes several commands or data such as an image simultaneously, and the CPU may be implemented in a structure having several cores specializing in a series processing method which processes in an order a command or data is input.

The processor 140 may be configured to control the deodorizing device 120 to perform deodorizing of removing the contaminant source of the clothing based on a user command for managing the clothing C being received, control the deodorizing device 120 to stop deodorizing based on the concentration of the contaminant source in the clothing management device 100 which is detected by the sensor 110 being determined as less than or equal to a pre-set threshold value, and control the perfuming device 130 to perform the perfuming of the clothing C by using the aroma.

Specifically, the processor 140 may be configured to control, based on a user command for managing the clothing C being received, the deodorizing device 120 to perform deodorizing of removing the contaminant source of the clothing C.

Here, the user command for managing the clothing C may be one from among the user command for performing the perfuming and the user command for performing deodorizing. That is, even when the user command for performing the perfuming is received, the clothing management device 100 may perform deodorizing prior to performing the perfuming. Meanwhile, the user command may be received through an input interface 150 (referring to FIG. 3) provided in the clothing management device 100, and for example, may be received in various forms such as a touch input through a display (touch sensor), a user voice input through a microphone, and a key input through a button-type key. In addition, the user command may be received from an external device (e.g., user terminal or server, etc.) to the processor 140 through a communication unit 180.

In addition, as described above with respect to the deodorizing device 120, the deodorization may be performed using at least one from among steam, air, and the photocatalyst, and the contaminant source present on the clothing C may be gradually removed according to the deodorization being performed. For example, the processor 140 may be configured to control the deodorizing device 120 to spray at least one from among steam and air toward the clothing C, and remove the contaminant source of the clothing C according thereto. Meanwhile, the processor 140 may be configured to control the deodorizing device 120 to irradiate light to the photocatalyst, and remove the contaminant source as the photocatalyst which is activated while light is being irradiated degrades the contaminant source of the clothing C to other substances.

The processor 140 may be configured to monitor the concentration of the contaminant source in the clothing management device 100 detected through the sensor 110. For example, the processor 140 may be configured to periodically monitor the concentration of the contaminant source in the clothing management device 100 detected through the sensor 110 while performing the deodorization on the clothing C.

According to another embodiment, the processor 140 may be configured to control, based on a user command being received, the deodorizing device 120 to first spray high-pressure air toward the clothing C.

In this case, the processor 140 may be configured to monitor the concentration of the contaminant source in the clothing management device 100 detected through the sensor 110. This is so that the sensor 110 may more accurately detect the concentration of the contaminant source by spraying high-pressure air to remove the contaminant source remaining on the clothing C while simultaneously diffusing the contaminant source inside of the clothing management device 100.

Then, the processor 140 may be configured to control the deodorizing device 120 to perform deodorization to remove the contaminant source of the clothing C.

As described above, the processor 140 may control the deodorizing device 120 to perform deodorization with respect to both of when the user command for performing the perfuming is received or when a user command for performing deodorization is received, and monitor the concentration of the contaminant source in the clothing management device 100 detected through the sensor 110.

Below, as an embodiment, a user command received by the processor 140 will be described assuming that it is the user command for performing the perfuming. Here, as described above with respect to the perfuming device 130, the perfuming may be performed by using at least one from among hot air, steam, a nozzle, and ultrasonic waves.

In this case, the processor 140 may be configured to control the deodorizing device 120 to stop deodorization based on determining that the concentration of the contaminant source in the clothing management device 100 which is detected by the sensor 110 is less than or equal to a pre-set threshold value. Further, the processor 140 may be configured to control the perfuming device 130 to perform the perfuming of the clothing C by using an aroma. In this case, the performing the perfuming after stopping (or ending) the deodorization is so that a fragrance of the aroma is not removed together therewith in the deodorization process.

That is, the processor 140 may be configured to control, based on the received user command being a command for performing the perfuming of the clothing C, deodorizing device 120 to stop deodorization based on determining that the concentration of the contaminant source is less than or equal to a pre-set threshold value, and perform the perfuming of the clothing C.

Here, the pre-set threshold value may be set to a value corresponding to a substance type of the contaminant source, and may be set to an experimentally determined value. This is because the threshold value on the odor recognized by the user according to the substance type may vary.

The processor 140 may end (or stop) deodorization when the concentration of the contaminant source reaches the target value based on the user command being the user command for performing deodorization, and the pre-set threshold value (e.g., 3 ppm) may be a value higher than the target value (e.g., 1 ppm) at which the deodorization is ended. In this case, the pre-set threshold value may be a value corresponding to a concentration which may cover the odor of the contaminant source through the fragrance of the aroma.

In addition, the pre-set threshold value may be set by a manufacturer of the clothing management device 100 or by the user, and it may also be possible for the pre-set threshold value to be changed by an update through the external device or by a user input.

Further, the processor 140 may be configured to control the perfuming device 130 to stop perfuming based on determining that the target value has been reached according to the concentration of the aroma in the clothing management device 100 which is detected by the sensor 110 increasing. That is, the processor 140 may be configured to control the perfuming device 130 to stop perfuming based on determining that the concentration of the aroma in the clothing management device 100 detected by the sensor 110 is greater than or equal to the target value.

Here, the target value may represent, as a concentration which is a reference to distinguishing whether the perfuming device 130 is to perform an operation of spraying the aroma to the clothing C or to stop operation of spraying the aroma, the concentration of the aroma to be achieved through perfuming.

The target value may be selected by the user. For example, the processor 140 may be configured to identify, through the input interface 150 or a communication unit 190, the target value according to the received user command when the user command inputting the target value itself is received or when the user command selecting one perfume level from among a plurality of perfume levels is received.

Here, the target value corresponding to a portion from among a plurality of target values may be pre-set to the perfume level. The target value on each perfume level may be set or changed by the user or the manufacturer. For example, the target value on perfume level 1 performing the perfuming of a weak degree may be set to 2 ppm, the target value on perfume level 2 performing the perfuming of an intermediate degree may be set to 5 ppm, and the target value on perfume level 3 performing the perfuming of a strong degree may be set to 8 ppm.

However, this is merely one embodiment, and the target value on each perfume level may be set to a value corresponding to the substance type of the aroma, and may be set to an experimentally determined value. This is also because the threshold value on the fragrance recognized by the user according to the substance type may vary.

For example, the processor 140 may be configured to identify, based on assuming that the user command selecting perfume level 1 is received, the target value (e.g., 2 ppm) corresponding to perfume level 1, and control the perfuming device 130 to stop perfuming based on determining that the target value (e.g., 2 ppm) has been reached according to the concentration of the aroma in the clothing management device 100 detected by the sensor 110 increasing.

According to an embodiment as described above, the concentration of the aroma fragrance to be coated on the clothing may be adjusted to a level desired by the user. In addition, as described above, the selecting of the target value through the perfume level may be simpler and more convenient than inputting the target value itself by the user, and information on the intensity of the perfuming degree may be provided more intuitively to the user through the perfume level.

According to an embodiment, the processor 140 may be configured to control the perfuming device 130 to perform drying and perfuming of the clothing C by using hot air after the deodorization is stopped. Here, the perfuming device 130 may include a heater which generates hot air (high-temperature air) and an air circulation device which supplies the hot air to the clothing management device 100.

Here, the processor 140 may be configured to control the perfuming device 130 to supply hot air into the clothing management device 100 along a first flow path, and adjust a valve connected to the first flow path so that at least a portion of the hot air moving along the first flow path is supplied into the clothing management device 100 through a second flow path at which the aroma is disposed. Here, the first flow path may refer to a path which connects the perfuming device 130 and the clothing management device 100 with each other and through which the hot air is moved. The second flow path may be configured such that the aroma is disposed and stored, and may be connected with the first flow path through the valve. The detailed description on the above will be described with reference to FIGS. 10A to 10C.

The processor 140 may be configured to control the perfuming device 130 to supply hot air into the clothing management device 100 along a plurality of flow paths, and the aroma may be disposed to at least one from among the plurality of flow paths. Here, the plurality of flow paths may refer to a path through which the hot air or steam is moved from the perfuming device 130 to the clothing management device 100. The detailed description on the above will be described with reference to FIGS. 11A and 11B.

Below, as another embodiment, the user command for performing deodorization will be described assuming that it has been received. That is, a user command for not performing the perfuming being received may be shown.

In this case, the processor 140 may be configured to control, based on the received user command being a command for not performing the perfuming of the clothing C, the deodorizing device 120 to proceed with deodorization until the concentration of the contaminant source detected by the sensor 110 reaches the target value which is lower than the pre-set threshold value. That is, in this case, the processor 140 may be configured to control, based on determining that the concentration of the contaminant source detected by the sensor 110 is less than or equal to the target value, the deodorizing device 120 to stop deodorization.

Here, the target value at which the deodorization is ended may be a value lower than the pre-set threshold value (e.g., 3 ppm). This is because the degree to which deodorization is performed to remove the odor of the contaminant source is greater since perfuming has not been performed.

Referring to FIG. 3, the electronic device (e.g., the clothing management device 100) may include, in addition to a sensor 110, a deodorizing device 120, a perfuming device 130, and a processor 140, at least one from among an input interface 150, an output interface 160, a memory 170, and a communication unit 180.

The input interface 150 may receive various user commands and transfer to the processor 140. That is, the user may input the user command to the clothing management device 100 through the input interface 150. Here, the user command may include various commands such as a command instructing to perform deodorization by the clothing management device 100, and a command instructing to perform deodorization and perfuming by the clothing management device 100.

The input interface 150 may include at least one from among, for example, a touch panel (not shown), a pen sensor (not shown), a key (not shown), and a microphone (not shown). The touch panel may use at least one method from among, for example, a capacitive type, a resistive type, an infrared method, or an ultrasonic method, and to this end the touch panel may include a control circuitry. The touch panel may further include a tactile layer, and provide a tactile response to the user. The pen sensor may be, for example a part of the touch panel, or include a separate sheet for recognition. The key may include, for example, a physical button, a photoionization key, or a keypad. The microphone may be configured to directly receive the user voice, and obtain an audio signal by converting the user voice which is an analog signal to a digital by a digital conversion unit (not shown).

The input interface 150 may be implemented as a form embedded in the clothing management device 100 as in the above-described description, but this is merely one embodiment, and the input interface 150 may also be implemented as a separate external device (not shown) such as a keyboard, a mouse, an external microphone, or a remote controller which is connected with the clothing management device 100 through wired or wireless communication (e.g., communication such as a universal serial bus (USB) method, a Bluetooth method, an infrared method, or the like).

The input interface 150 may be disposed at an inner side surface or an outer side surface of the clothing management device 100, and may be disposed, for example, at one side surface of a door of the clothing management device 100.

The output interface 160 may be configured to output information detected by the sensor 110 in various types such as visual or auditory, information processed through the processor 140, and information corresponding to the user command which is input through the input interface 150. That is, the user may recognize the information output through the output interface 160 and interact with the clothing management device 100.

The output interface 160 may be implemented as, for example, a display, a speaker, or the like. Here, the display may be a device configured to output information or data visually. The display may display an image frame at a whole or part of an area of a display area. The display area may refer to the whole area of a pixel unit at which the information or data is visually displayed. At least a portion of the display may be coupled to at least one for among a front surface area, a side surface area, and a rear surface area of the clothing management device 100 in the form of a flexible display. The flexible display may be characterized by being bendable, twistable or rollable without damage through a substrate which is thin and flexible like paper. In addition, the speaker may output not only various audio data performed with various processing work such as decoding or amplification, noise filtering or the like by an audio processing unit (not shown), but also various notification sounds or voice messages directly to sound, and may be implemented in a form embedded in the clothing management device 100 or implemented to a separate external device which is connected with the clothing management device 100 through wired and wireless communication. In addition, it may also be possible for the speaker to be implemented as a directional speaker transferring sound to only a specified location or area.

The memory 170 may refer to a hardware storing data or information temporarily or permanently. For example, the memory 170 may be implemented as at least one hardware from among a non-volatile memory, a volatile memory, a flash memory, a hard disk drive (HDD) or a solid state drive (SDD), a random access memory (RAM), a read only memory (ROM), or the like.

The memory 170 may be stored with at least one instruction, program, or data necessary in an operation of the clothing management device 100 or the processor 140. Here, the instruction may be a code unit instructing an operation of the clothing management device 100 or the processor 140, and may be prepared in a mechanical language which is a language understood by a computer. The program may be a series of instruction set performing a specific work of a work unit. The data may be state information in a bit or byte unit capable of representing characters, numbers, images, and the like.

In addition, the memory 170 may be stored with various information such as information detected by the sensor (e.g., concentration of the contaminant source or the aroma), information processed by the processor 140, and information on an operation being performed by the clothing management device 100. The information stored in the memory 170 may be accessed by the processor 140, and for example, reading/writing/modifying/deleting/updating or the like on the instruction, program or data stored in the memory 170 may be performed by the processor 140.

The communication unit 180 may be configured to transmit and receive data of various types with an external device of various types (e.g., a user terminal device such as a smartphone, a server, or the like) according to various wired or wireless communication methods. At this time, the communication unit 180 may perform direct communication with the external device, or perform communication with the external device via (or relaying) another external device through various communication networks.

The communication unit 180 may be configured to receive information from the external device, and transfer the received information to the processor 140. For example, the communication unit 180 may be configured to receive the user command from the user terminal device (or server).

In addition, the communication unit 180 may be configured to transmit information to the external device according to the control of the processor 140. For example, the communication unit 180 may be configured to transmit information on the operation currently being performed by the clothing management device 100 or information detected through the sensor 110 of the clothing management device 100 to the user terminal device (or server) according to the control of the processor 140.

To this end, the communication unit 180 may include a network interface or a network chip according to the wired and wireless communication method. Here, the network interface may include circuitry according to each communication method, and may further include an antenna or the like in the case of the wireless communication method. For example, the communication unit 180 may include at least one from among a wireless fidelity (Wi-Fi) chip using a Wi-Fi communication method, a Bluetooth chip using a Bluetooth communication method, an NFC chip using a near field communication (NFC) communication method, a wireless communication chip using a mobile communication method (e.g., long-term evolution (LTE), LTE Advanced (LTE-A), 5th Generation (5G), code division multiple access (CDMA), wideband CDMA (WCDMA)), and an infrared communication chip using an infrared communication method. Further, the communication unit 180 may include at least one from among an Ethernet module (not shown) and a universal serial bus (USB) module (not shown) performing wired communication. Meanwhile, the communication unit 180 is not limited to the above-described examples, and may be modified to perform communication based on newly appearing communication methods according to the development of technology.

The clothing management device 100 according to an embodiment may be configured to receive the user command from the user terminal device which is network connected through the communication unit 180, or may be implemented in a form outputting information from the user terminal device by transmitting information to the user terminal device. At this time, the user terminal device may include the above-described input interface 150 or the output interface 160.

Figure 4:
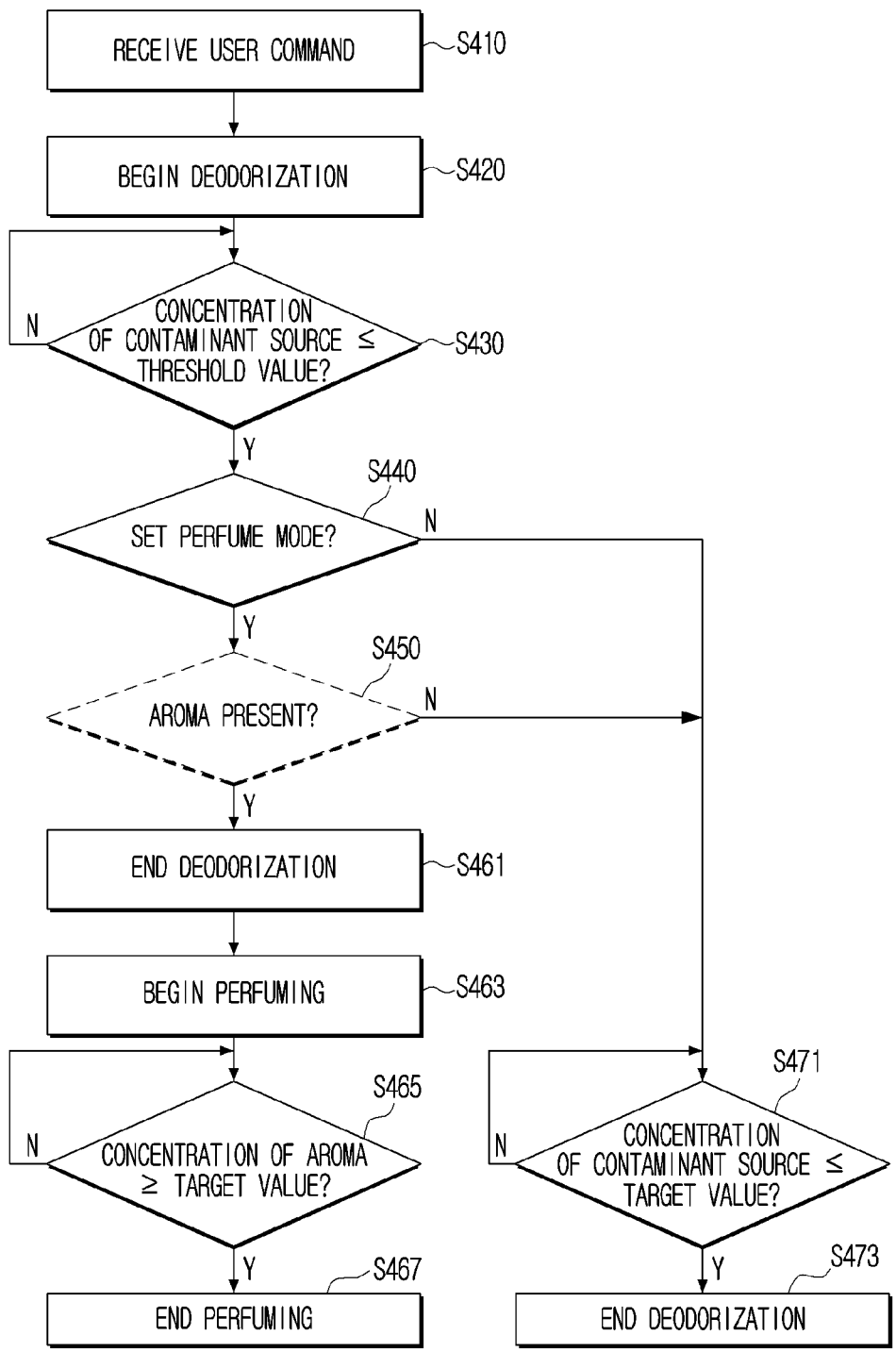
FIG. 4 is a diagram illustrating an operation of a clothing management device according to an embodiment of the disclosure.

FIG. 4 is a diagram illustrating an operation of a clothing management device according to an embodiment of the disclosure. Here, the parts overlapping with the above-described descriptions will be briefly described.

Referring to FIG. 4, a clothing management device 100 may be configured to receive the user command for managing clothing, at operation S410. The user command may be received through various methods such as a touch input, a user voice input, a key input, and an input through a network communication. In addition, the user command may be one from among a command for performing the perfuming (perfume mode or perfuming course, etc.) or a command for performing deodorization (deodorizing mode or deodorizing course, etc.).

In this case, the clothing management device 100 may be configured to perform deodorization of removing the contaminant source of the clothing through the deodorizing device 120, at operation S420.

In this case, the clothing management device 100 may be configured to detect the concentration of the contaminant source periodically through the sensor 110, and periodically determine whether the concentration of the contaminant source in the clothing management device 100 is less than or equal to the pre-set threshold value, at operation S430.

Then, the concentration of the contaminant source in the clothing management device 100 may gradually reduce according to the deodorization being performed. Further, the clothing management device 100 may be configured to determine, based on determining that the concentration of the contaminant source in the clothing management device 100 is less than or equal to the pre-set threshold value at operation S430, Y, which command from among the command for performing (perfume mode) and the command for performing deodorization (deodorizing mode) the user command is that is received in operation S410, in operation S440. Different from the above, the clothing management device 100 may continue to proceed with deodorization based on determining that the concentration of the contaminant source in the clothing management device 100 exceeded the pre-set threshold value at operation S430, N.

In an embodiment, the clothing management device 100 may end (or stop), based on determining that the user command is the command for performing the perfuming (perfume mode; at operation S440, Y), the deodorization being performed, at operation S461. Meanwhile, the clothing management device 100 may be configured to detect, based on the user command being the command for performing the perfuming (perfume mode; at operation S440, Y), the aroma for performing the perfuming through the sensor 110, at operation S450. The clothing management device 100 may be configured to end (or stop), based on determining that the aroma for performing the perfuming is present at operation S450, Y, the deodorization being performed, at operation S461.

Then, when the deodorization is ended at operation S461, the clothing management device 100 may be configured to begin perfuming of the clothing using the aroma, at operation S463.

In this case, the clothing management device 100 may be configured to detect the concentration of the aroma in the clothing management device 100 periodically through the sensor 110, and the clothing management device 100 may be configured to periodically determine whether the concentration of the aroma in the clothing management device 100 is greater than or equal to the target value, at operation S465. At this time, the target value may be identified according to the user command received at operation S410. That is, the user command received at operation S410 may be a command inputting the target value itself or the user command selecting the perfume level. With respect to each perfume level, the target value may be pre-set.

Then, the concentration of aroma may be gradually increased according to proceeding with the perfuming. Further, the clothing management device 100 may be configured to end, based on determining that the concentration of aroma is greater than or equal to the target value at operation S465, Y, the perfuming being performed, at operation S467. Different from the above, the clothing management device 100 may be configured to continue performing the perfuming based on determining that the concentration of aroma is less than the target value, at operation S465, N.

In another embodiment, the clothing management device 100 may be configured to continue performing deodorization based on the user command being the command for not performing the perfuming at operation S440, N, or determining that the aroma for performing the perfuming is not present, at operation S450, N.

That is, the clothing management device 100 may be configured to proceed with deodorization until the concentration of the contaminant source detected by the sensor 110 reaches the target value. At this time, the target value may be a value lower than the pre-set threshold value.

In this case, the clothing management device 100 may be configured to detect the concentration of the contaminant source periodically through the sensor 110, and periodically determine whether the concentration of the contaminant source is less than or equal to the target value, at operation S471.

Then, the concentration of the contaminant source may be gradually reduced according to proceeding with deodorization. Further, the clothing management device 100 may be configured to end (or stop), based on determining that the concentration of the contaminant source is less than or equal to the target value at operation S471, Y, the deodorization being performed, at operation S473. Different from the above, the clothing management device 100 may be configured to continue performing the deodorization based on determining that the concentration of the contaminant source exceeded the target value, at operation S471, N.

Meanwhile, the above-described embodiment is merely an embodiment, and variously modified embodiments may be possible. For example, the part shown with dotted lines in FIG. 4 is an additional operation which may be omitted, and may be various modified such as the order of each operation being changed or new operations being added.

Figure 5:
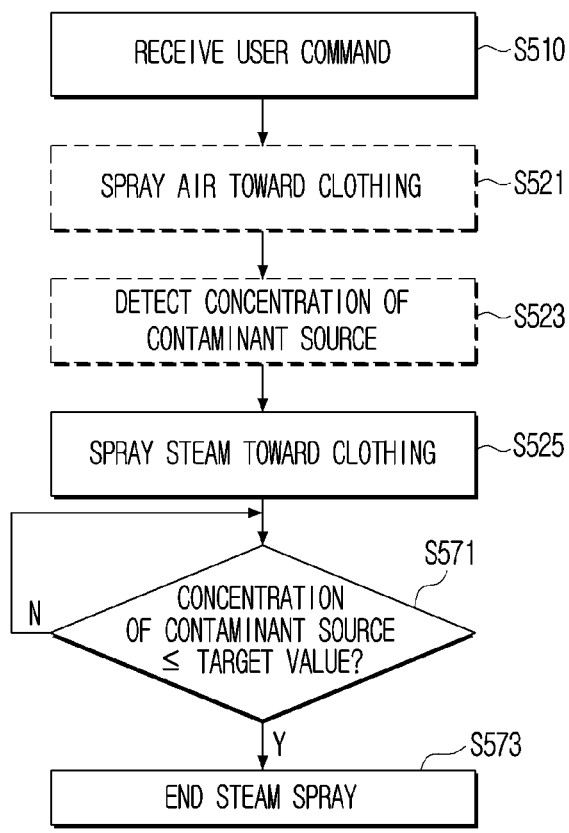
FIG. 5 is a diagram illustrating deodorization according to an embodiment of the disclosure.
Figure 6:
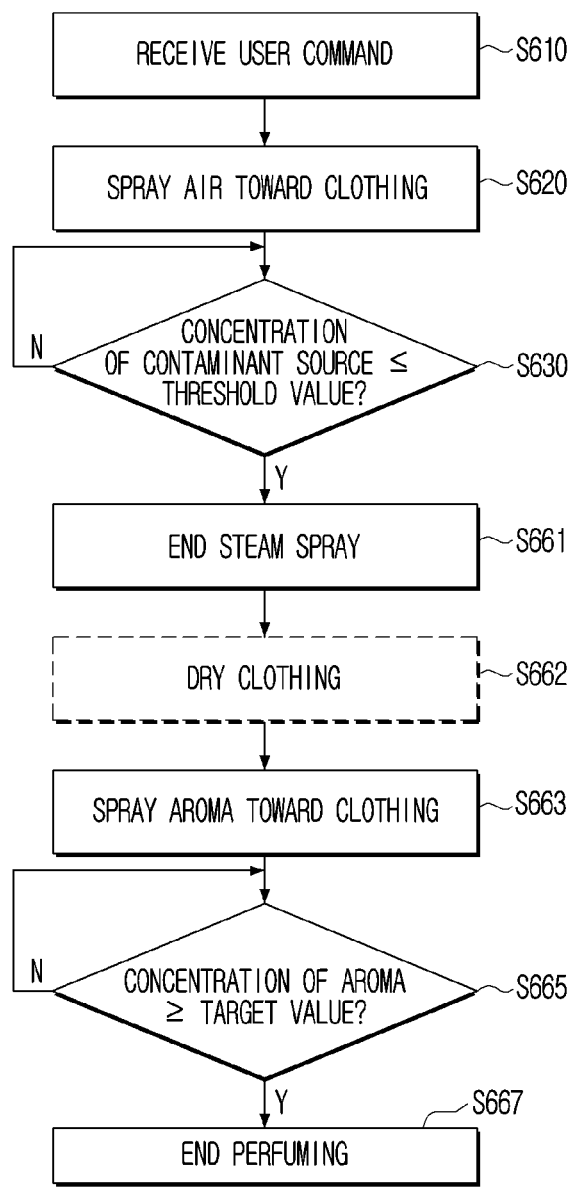
FIG. 6 is a diagram illustrating perfuming according to an embodiment of the disclosure.

FIG. 5 is a diagram illustrating deodorization according to an embodiment of the disclosure, and FIG. 6 is a diagram illustrating perfuming according to an embodiment of the disclosure. Here, parts overlapping with the above-described descriptions will be briefly described.

Referring to FIG. 5, a clothing management device 100 according to an embodiment may be configured to spray, based on the user command for performing deodorization (deodorizing mode or deodorizing course, etc.) being received at operation S510, air toward the clothing through the deodorizing device 120, at operation S521. Accordingly, the contaminant source present at a fabric surface or a gap of the clothing may be separated from the clothing and diffused into the clothing management device 100.

In this case, the clothing management device 100 may be configured to detect the concentration of the contaminant source in the clothing management device 100 through the sensor 110, at operation S523. Accordingly, the concentration of the contaminant source in the clothing management device 100 may be more accurately detected.

Further, the clothing management device 100 may be configured to spray steam toward the clothing through the deodorizing device 120, at operation S525. Accordingly, the contaminant source present on the clothing or the contaminant source diffused in the clothing management device 100 may be dissolved by steam and the contaminant source may be removed. At this time, the steam which dissolved the contaminant source may be collected in the water tank provided in the clothing management device 100. In addition, in this case, the clothing management device 100 may activate the photocatalyst through the deodorizing device 120, and remove the contaminant source by the activated photocatalyst.

In this case, the clothing management device 100 may be configured to periodically detect the concentration of the contaminant source in the clothing management device 100 through the sensor 110, and periodically determine whether the concentration of the contaminant source is less than or equal to the target value, at operation S571.

Then, the clothing management device 100 may be configured to end (or stop), based on determining that the concentration of the contaminant source is less than or equal to the target value at operation S571, Y, the deodorization being performed by the deodorizing device 120, at operation S573.

Referring to FIG. 6, a clothing management device 100 according to an embodiment may be configured to spray, based on receiving the user command for performing the perfuming (perfume mode or perfume course, etc.), at operation S610, steam (or air, etc.) toward the clothing through the deodorizing device 120, at operation S620. Accordingly, the concentration of the contaminant source may be reduced.

In this case, the clothing management device 100 may be configured to detect the concentration of the contaminant source periodically through the sensor 110, and periodically determine whether the concentration of the contaminant source in the clothing management device 100 is less than or equal to the pre-set threshold value, at operation S630.

Further, the clothing management device 100 may be configured to stop (or end), based on determining that the concentration of the contaminant source in the clothing management device 100 is less than or equal to the pre-set threshold value at operation S630, Y, the operation of spraying steam by the deodorizing device 120, at operation S661.

Then, when spraying steam is ended, the clothing management device 100 may be configured to spray hot air toward the clothing through the perfuming device 130, at operation S662. This is to dry the clothing dampened by the steam.

In addition, the clothing management device 100 may be configured to spray the aroma toward the clothing through the perfuming device 130, at operation S663. At this time, the aroma may be sprayed by various methods such as hot air, steam, spray, and ultrasonic waves.

In this case, the clothing management device 100 may be configured to detect the concentration of the aroma in the clothing management device 100 periodically through the sensor 110, and the clothing management device 100 may periodically determine whether the concentration of the aroma in the clothing management device 100 is greater than or equal to the target value, at operation S665.

Further, the clothing management device 100 may be configured to end, based on the concentration of the aroma being determined as greater than or equal to the target value at operation S465, Y, perfuming being performed by the perfuming device 130, at operation S667.

Meanwhile, the above-described embodiment is merely an embodiment, and variously modified embodiments may be possible. For example, the parts shown with dotted lines in FIGS. 5 and 6 are additional operations which may be omitted, and may be various modified such as the order of each operation being changed or new operations being added.

Figure 7:
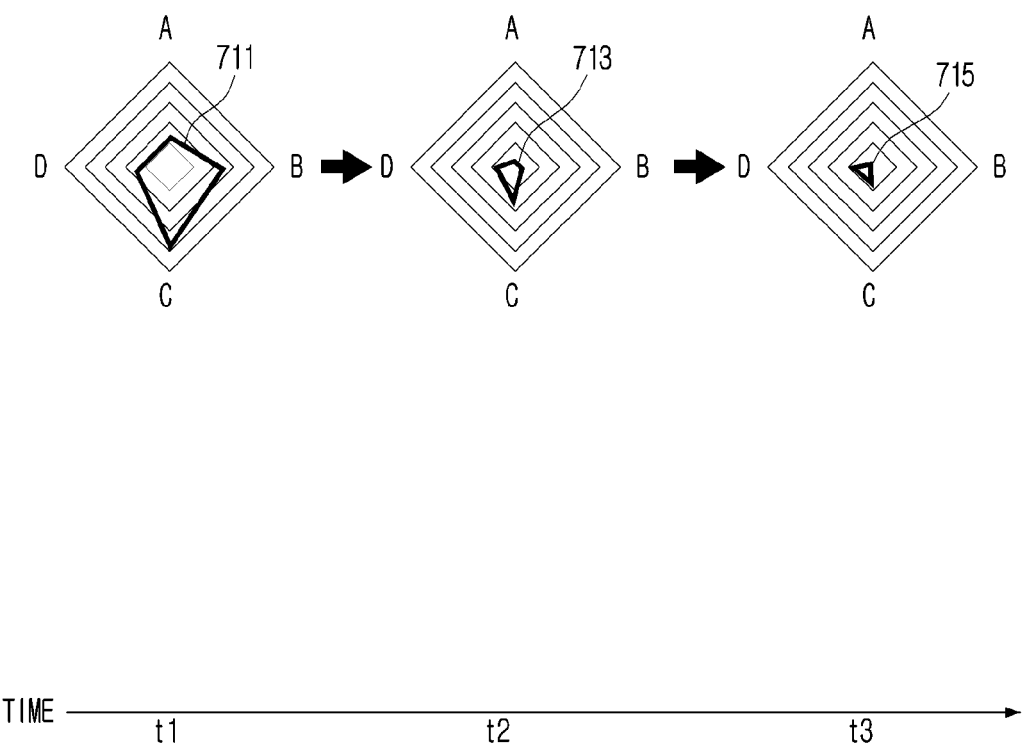
FIG. 7 is a diagram illustrating a concentration of a contaminant source based on deodorization according to an embodiment of the disclosure.

FIG. 7 is a diagram illustrating a concentration of a contaminant source based on deodorization according to an embodiment of the disclosure.

Referring to FIGS. 4 and 7, a user command for performing deodorization (deodorizing mode or deodorizing course) being received will be described. Here, it may be assumed that the contaminant source may be on a plurality of contaminant sources (contaminant source materials A to D).

First, as in operation S420, based on being at a first time point t1 at which the deodorization has begun (started) by the clothing management device 100, a concentration 711 of the contaminant source may be detected through the sensor 110 as, for example, contaminant source A being 3 ppm, contaminant source B being 5 ppm, contaminant source C being 8 ppm, and contaminant source D being 3 ppm.

Then, based on being at a second time point t2 at which the concentration of the contaminant source is reduced with the progress of deodorization, a concentration 713 of the contaminant source may be detected through the sensor 110 as, for example, contaminant source A being 1 ppm, contaminant source B being 1 ppm, contaminant source C being 4 ppm, and contaminant source D being 2 ppm.

In this case, the processor 140 may be configured to determine whether the concentration 713 of the contaminant source has reached the threshold value, at operation S430. For example, various methods such as comparing a relationship in magnitude between the concentration of each of the plurality of contaminant sources and the pre-set threshold value (comparing by a plurality of times), comparing the relationship in magnitude between an average in concentration of the plurality of contaminant sources and the pre-set threshold value (comparing by number of times of one time), comparing the relationship in magnitude between an area with respect to concentrations 711, 713 and 715 of the contaminant source (area of the figures shown in the graph) and the pre-set threshold value (comparing by number of times of one time), or the like, may be used.

Below, the concentration 713 of the contaminant source at the second time point t2 will be described assuming that it has reached the threshold value. In this case, the processor 140 may be configured to determine that the concentration of the contaminant source at the second time point t2 has reached the threshold value at operation S430, Y, and determine whether the received user command is a command for performing the perfuming, at operation S440. Further, according to the above-described assumption, the processor 140 may be configured to determine the received user command as the user command for not performing the perfuming at operation S440, N, and continue to proceed with deodorization.

Then, based on being at a third time point t3 at which the concentration of the contaminant source is reduced with the progress of deodorization, a concentration 715 of the contaminant source may be detected through the sensor 110 as, for example, contaminant source A being 0.1 ppm, contaminant source B being 0.1 ppm, contaminant source C being 1 ppm, and contaminant source D being 1 ppm.

In this case, the processor 140 may be configured to determine whether the concentration 715 of the contaminant source has reached the target value, at operation S471. Because the above overlaps with the above-described description, the description will be omitted.

Below, the concentration 715 of the contaminant source at the third time point t3 will be described assuming that it has reached the target value. In this case, the processor 140 may be configured to determine that the concentration of the contaminant source at the third time point t3 has reached the target value at operation S471, Y, and control the deodorizing device 120 to end deodorization, at operation S473.

Figure 8:
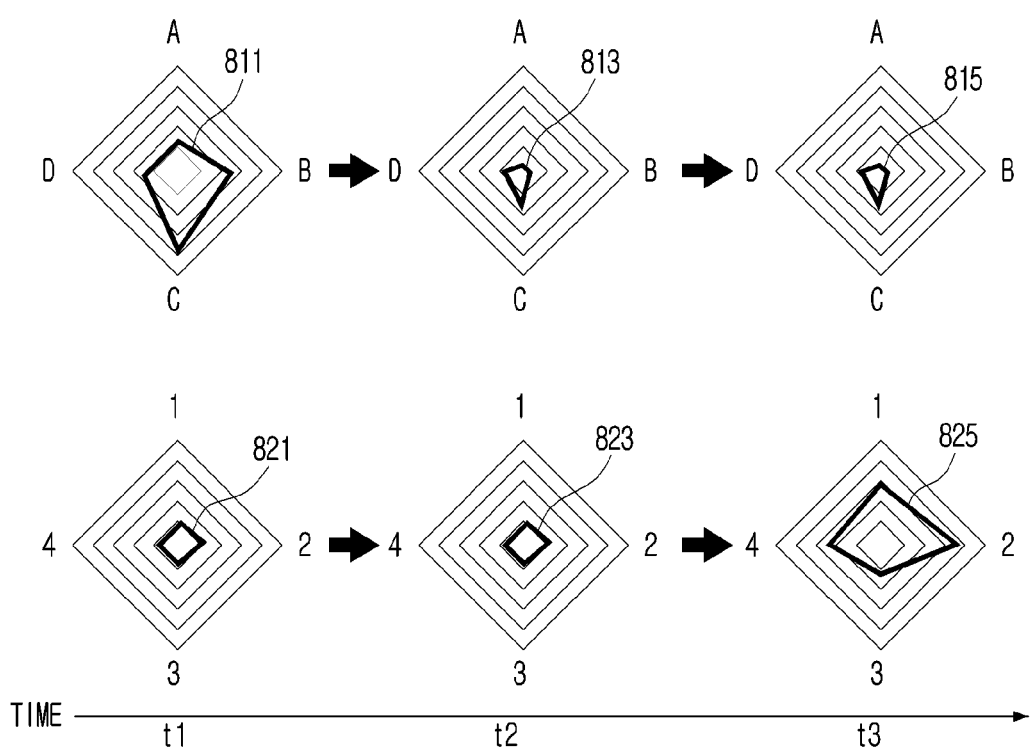
FIG. 8 is a diagram illustrating a concentration of an aroma based on perfuming according to an embodiment of the disclosure.

FIG. 8 is a diagram illustrating a concentration of an aroma based on perfuming according to an embodiment of the disclosure.

Referring to FIGS. 4 and 8, a user command for performing the perfuming (perfume mode or perfume course) being received will be described. Here, it may be assumed that the contaminant source may be on a plurality of contaminant sources (contaminant source materials A to D), and the aroma may be on a plurality of aromas (aroma materials 1 to 4).

First, as in operation S420, based on being at the first time point t1 at which the deodorization has begun (started) by the clothing management device 100, a concentration 811 of the contaminant source may be detected through the sensor 110 as in FIG. 8. At this time, a concentration 821 of the aroma may also be detected through the sensor 110.

Then, based on being at the second time point t2 at which the concentration of the contaminant source is reduced with the progress of deodorization, a concentration 813 of the contaminant source may be detected as having reduced compared to the previous time point through the sensor 110 as in FIG. 8. At this time, based on perfuming not being performed, a concentration 823 of the aroma detected through the sensor 110 may not be different from the concentration 821 of the aroma detected at the first time point t1.

In this case, the processor 140 may be configured to determine whether the concentration 813 of the contaminant source has reached the threshold value, at operation S430. Here, the concentration 813 of the contaminant source at the second time point t2 will be described assuming that it has reached the threshold value.

In this case, the processor 140 may be configured to determine that the concentration of the contaminant source at the second time point t2 has reached the threshold value at operation S430, Y, and determine whether the received user command is the command for performing the perfuming, at operation S440. Further, according to the above-described assumption, the processor 140 may be configured to determine the received user command as the user command for performing the perfuming at operation S440, Y, control the deodorizing device 120 to stop deodorization at operation S461, and control the perfuming device 130 to begin perfuming, at operation S463.

Then, based on being at the third time point t3 at which the concentration of the aroma is increased with the progress of perfuming, a concentration 825 of the aroma may be detected as having increased compared to the previous time point through the sensor 110. At this time, a concentration 815 of the contaminant source may be detected through the sensor 110, and change with respect to the concentration may be slight compared to the previous time point based on the deodorization not being performed.

In this case, the processor 140 may be configured to determine whether the concentration 825 of the aroma has reached the target value, at operation S465. The above will be omitted in that the above-described description on the concentration of the contaminant source may be applied.

Below, the concentration 825 of the aroma at the third time point t3 will be described assuming that it has reached the target value. In this case, the processor 140 may be configured to determine that the concentration 825 of the aroma at the third time point t3 has reached the target value at operation S465, Y, and control the perfuming device 130 to end perfuming, at operation S467.

Figure 9:
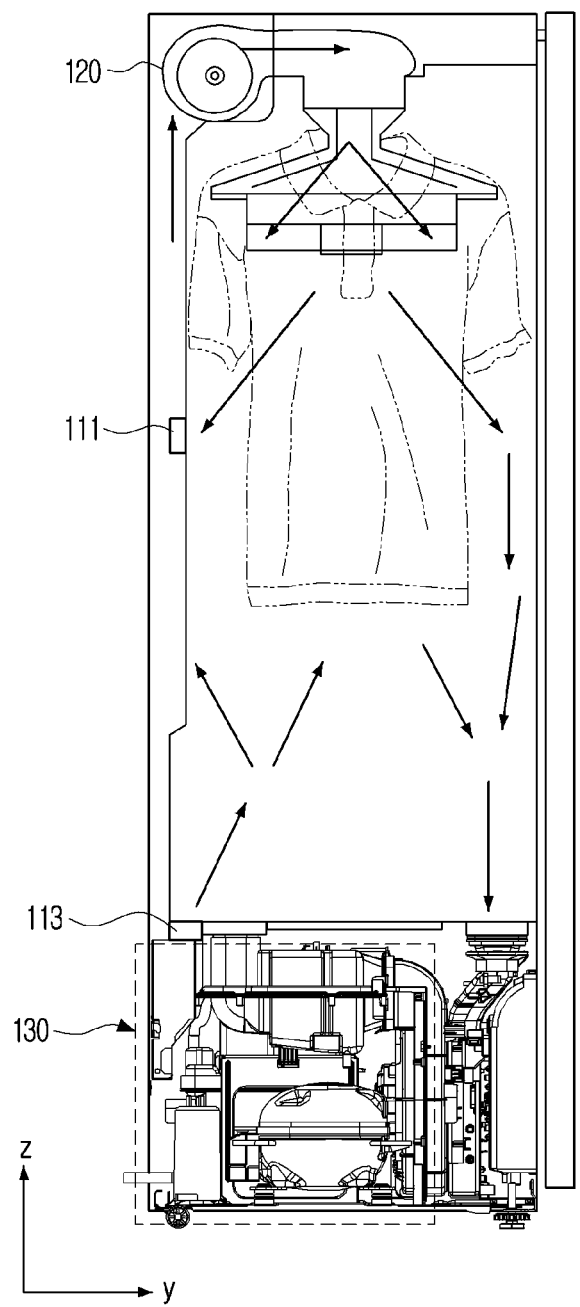
FIG. 9 is a diagram illustrating a gas flow according to an embodiment of the disclosure.

FIG. 9 is a diagram illustrating a gas flow according to an embodiment of the disclosure.

Referring to FIG. 9, a deodorizing device 120 according to an embodiment may be disposed at an upper end part of a clothing management device 100. In this case, the deodorizing device 120 may be configured to spray high-pressure air (or steam) generated through the compressor (or steam generator) toward the clothing C through the discharging member. Here, the discharging member may be formed at an upper end or inside of the clothing support at which the clothing is to be laid, and accordingly, high-pressure air may be sprayed from the upper end of the clothing C to a lower end of the clothing C, or sprayed from the inside of the clothing C toward the outside of the clothing C.

In this case, the clothing management device 100 may be formed with an inlet or an outlet at various locations.

In an embodiment, air inside of the clothing management device 100 may be introduced to the compressor of the deodorizing device 120 through the outlet formed at one side surface of the clothing management device 100. In addition, a separate filter may be installed at the outlet, and accordingly, the contaminant source or dust present in air which is introduced to the compressor may be removed. Further, the first gas sensor 111 for measuring the concentration of the contaminant source may be disposed around the outlet.

In another embodiment, air inside the clothing management device 100 may be introduced to the perfuming device 130 through the outlet formed at the lower end part of the internal space of the clothing management device 100. In addition, a separate filter may be installed at the outlet, and accordingly, the contaminant source or dust present in air which is introduced to the perfuming device 130 may be removed.

The perfuming device 130 according to an embodiment may be configured to generate hot air (high-temperature air), and spray the hot air through the inlet formed at the lower end part of the internal space of the clothing management device 100 in a direction of the clothing C. In this case, the perfuming device 130 may be configured to dry the clothing C by removing the moisture present on the clothing C by continuously circulating the high-temperature air inside of the clothing management device 100.

In addition, the perfuming device 130 according to an embodiment may spray the aroma together with hot air (or steam) in the direction of the clothing C through the inlet. In this case, the second gas sensor 113 for measuring the concentration of the aroma may be disposed around the inlet.

As described above, the perfuming device 130 according to an embodiment may dry the clothing C through hot air while simultaneously spraying the aroma, and coat the fragrance corresponding to the aroma on the clothing.

In this case, the amount (concentration or intensity) of the aroma being sprayed on the clothing C may be controlled to a level desired by the user, and to this end, there is a need to adjust a flow rate of gas (hot air or steam) being supplied toward the aroma which is disposed at the flow path that connects between the insides of the perfuming device 130 and the clothing management device 100. Below, a method of adjusting the flow rate of gas (hot air or steam) being supplied toward the aroma which is disposed at the flow path will be described with reference to FIGS. 10A to 10C, 11A, and 11B.

Figure 10A:
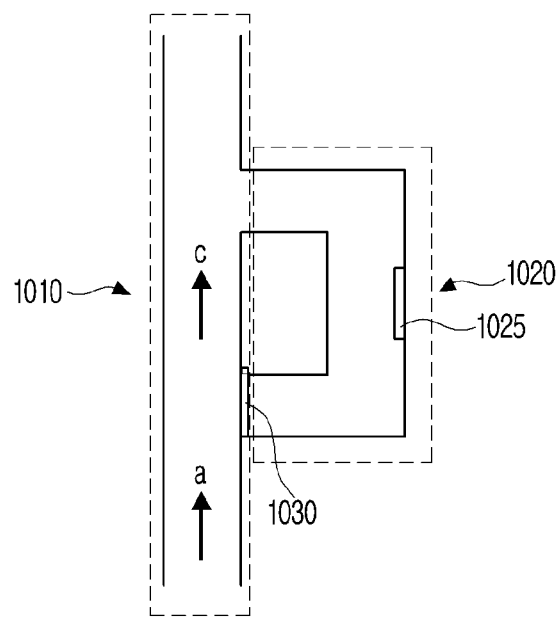
FIG. 10A is a diagram illustrating a method of adjusting a gas flow according to an embodiment of the disclosure.
Figure 10B:
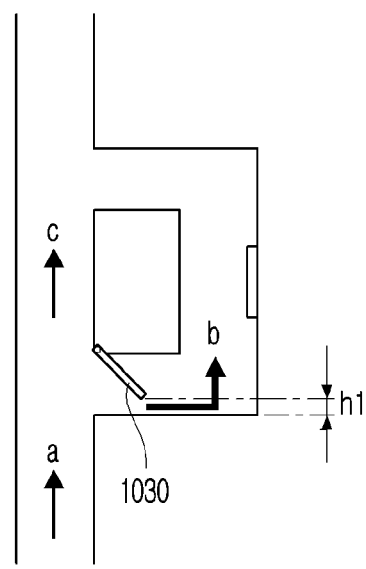
FIG. 10B is a diagram illustrating a method of adjusting a gas flow according to an embodiment of the disclosure.
Figure 10C:
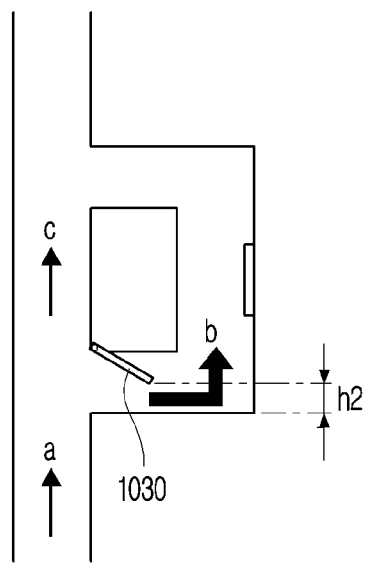
FIG. 10C is a diagram illustrating a method of adjusting a gas flow according to an embodiment of the disclosure.

FIGS. 10A, 10B, and 10C are diagrams illustrating a method of adjusting a gas flow according to various embodiments of the disclosure.

Referring to FIGS. 10A to 10C, a processor 140 may be configured to control, based on performing drying or perfuming of the clothing C, a perfuming device 130 to supply hot air into a clothing management device 100 along a first flow path 1010.

In addition, the processor 140 may be configured to adjust a valve 1030 connected to the first flow path 1010. Accordingly, at least a portion of the hot air which moves along the first flow path 1010 may be supplied into the clothing management device 100 through a second flow path 1020 at which aroma 1025 is disposed, or the hot air which moves along the first flow path 1010 may be supplied into the clothing management device 100 without passing the second flow path 1020.

Here, the first flow path 1010 may connect the perfuming device 130 and the clothing management device 100 with each other, and may refer to a path through which hot air is moved. The second flow path 1020 may be disposed with the aroma 1025 and stored, and may connect with the first flow path through the valve 1030.

For example, as in FIG. 10A, the processor 140 may be configured to control the perfuming device 130 to supply hot air into the clothing management device 100 along the first flow path 1010, and adjust the valve 1030 connected to the first flow path 1010 so that the hot air which moves along the first flow path 1010 is supplied into the clothing management device 100 without passing the second flow path 1020 at which the aroma 1025 is disposed. That is, the processor 140 may be configured to adjust the valve 1030 such that the flow of hot air is blocked between the first flow path 1010 and the second flow path 1020. Accordingly, the clothing management device 100 of the disclosure may be configured to perform only drying of the clothing C without perfuming of the clothing C.

For example, as in FIGS. 10B and 10C, the processor 140 may be configured to control the perfuming device 130 to supply hot air into the clothing management device 100 along the first flow path 1010, and adjust the valve 1030 connected to the first flow path 1010 such that at least a portion of the hot air which moves along the first flow path 1010 is supplied into the clothing management device 100 through the second flow path 1020 at which the aroma 1025 is disposed. Accordingly, the clothing management device 100 of the disclosure may be configured to perform drying of the clothing while simultaneously performing the perfuming of the clothing.

Here, as in FIGS. 10B and 10C, the processor 140 may be configured to adjust the degree of the valve 1030 being opened and closed or the degree of the valve 1030 being rotated. At this time, according to the degree of the valve 1030 being opened and closed or the degree of the valve 1030 being rotated, cross-sectional areas h1 and h2 of the flow path may be determined. That is, by adjusting the flow rate of hot air being supplied to the second flow path 1020 at which the aroma 1025 is disposed, the amount of aroma 1025 being sprayed into the clothing management device 100 may be adjusted.

For example, based on the cross-sectional area h2 of the second flow path 1020 which is opened by the valve 1030 as in FIG. 10C being greater than the cross-sectional area h1 of the second flow path 1020 which is opened by the valve 1030 as in FIG. 10B, the flow rate of hot air supplied to the second flow path 1020 at which the aroma 1025 is disposed may increase in the case of FIG. 10C than in the case of FIG. 10B.

According to an embodiment of the disclosure as described above, the drying function and the perfuming function may be performed independently from each other by using a device capable of performing the drying function, and there is the effect of being able to perform the perfuming to a level desired by the user.

Figure 11A:
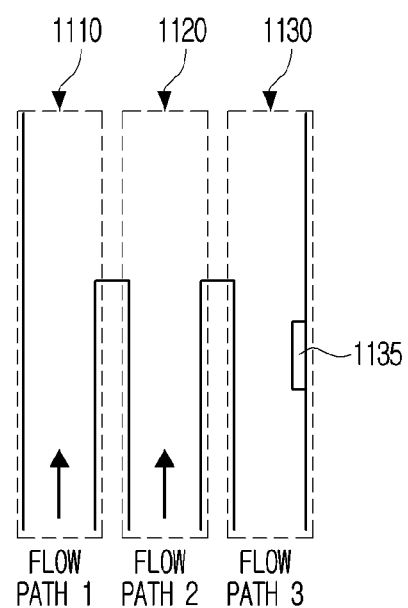
FIG. 11A is a diagram illustrating a method of adjusting a gas flow according to an embodiment of the disclosure.
Figure 11B:
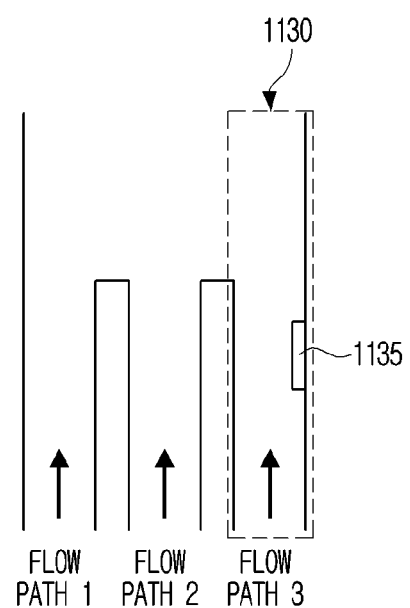
FIG. 11B is a diagram illustrating a method of adjusting a gas flow according to an embodiment of the disclosure.

FIGS. 11A and 11B are diagrams illustrating a method of adjusting a gas flow according to various embodiments of the disclosure.

Referring to FIGS. 11A and 11B, a processor 140 may be configured to control a perfuming device 130 to supply hot air into the clothing management device 100 along a plurality of flow paths 1110, 1120, and 1130, and an aroma 1135 may be disposed in at least one flow path 1130 from among the plurality of flow paths 1110, 1120, and 1130.

Here, the plurality of flow paths 1110, 1120, and 1130 may refer to paths through which hot air or steam is moved from the perfuming device 130 to the clothing management device 100. In addition, the aroma 1135 may be disposed in at least one flow path 1130 from among the plurality of flow paths 1110, 1120, and 1130.

In this case, the processor 140 may be configured to control the perfuming device 130 to supply hot air into the clothing management device 100 along the plurality of flow paths 1110, 1120, and 1130. At this time, the processor 140 may be configured to control the perfuming device 130 to supply hot air (or steam) into the clothing management device 100 along at least one flow path 1130 at which the aroma 1135 is disposed.

For example, as in FIG. 11A, the processor 140 may be configured to control the perfuming device 130 to supply hot air into the clothing management device 100 along the remaining flow paths 1010 and 1020 at which the aroma 1135 is not disposed, excluding the at least one flow path 1130 at which the aroma 1135 is disposed. Accordingly, the clothing management device 100 of the disclosure may be configured to perform only the drying of the clothing C without perfuming of the clothing C.

For example, referring to FIG. 11B, the processor 140 may be configured to control the perfuming device 130 to supply hot air into the clothing management device 100 along the flow paths 1010 and 1020 at which the aroma 1135 is not disposed. In addition, the processor 140 may be configured to control the perfuming device 130 to supply hot air (or steam) into the clothing management device 100 along the at least one flow path 1130 at which the aroma 1135 is disposed. In this case, the aroma may be vaporized (or dissolved) in the hot air (or steam) supplied to the at least one flow path 1130 at which the aroma 1135 is disposed and supplied into the clothing management device 100. Accordingly, the clothing management device 100 of the disclosure may be configured to perform drying of the clothing C while simultaneously performing the perfuming of the clothing C.

Referring to FIG. 11B, the processor 140 may be configured to control the perfuming device 130 to adjust the amount of hot air (or steam) supplied to at least one flow path 1130 at which an aroma 1135 is disposed, and in this case, the amount of aroma 1135 being sprayed into the clothing management device 100 may be adjusted.

FIG. 12 is a diagram illustrating a contaminant source according to an embodiment of the disclosure.

Referring to FIG. 12, a contaminant source may include at least one from among the substances (or compounds) disclosed in the table of FIG. 12, and each substance may have a chemical formula, a characteristic of the odor, an odor threshold, a characteristic of a molar mass disclosed in a same row.

However, the embodiment on the contaminant source described in FIG. 12 is merely one embodiment, and the contaminant source may include a gaseous substance, a volatile compound, and the like which causes an odor (malodor) giving displeasure and aversion by stimulating the olfactory sense of the typical user.

Figure 13:
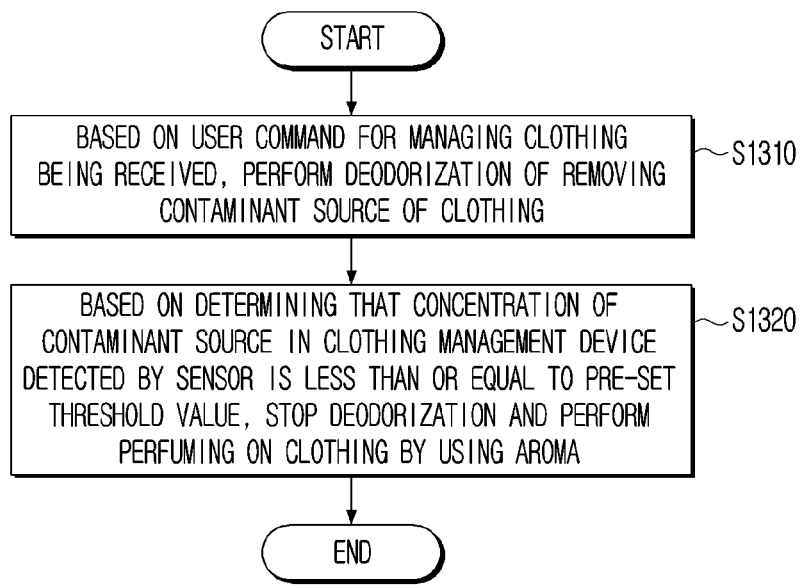
FIG. 13 is a diagram illustrating a flowchart according to an embodiment of the disclosure.

FIG. 13 is a diagram illustrating a flowchart according to an embodiment of the disclosure.

Referring to FIG. 13, a control method of a clothing management device 100 according to an embodiment of the disclosure may include performing, based on the user command for managing the clothing being received, deodorization of removing the contaminant source of the clothing C which is contained in the clothing management device 100, at operation S1310, and stopping, based on determining that the concentration of the contaminant source in the clothing management device 100 which is detected by the sensor 110 is less than or equal to the pre-set threshold value, deodorization and performing the perfuming of the clothing C by using the aroma, at operation S1320.

First, based on the user command for managing the clothing C being received, deodorization of removing the contaminant source of the clothing C which is contained in the clothing management device 100 may be performed, at operation S1310. Here, the received user command may be the command for performing the perfuming of the clothing or the command for not performing the perfuming of the clothing.

Here, the performing deodorization may include removing the contaminant source of the clothing C by spraying steam toward the clothing C.

Then, based on determining that the concentration of the contaminant source in the clothing management device 100 which is detected by the sensor 110 is less than or equal to the pre-set threshold value, stop deodorization and perform the perfuming of the clothing C by using the aroma, at operation S1320.

In an embodiment, the performing the perfuming may include performing the perfuming of the clothing C based on determining that the concentration of the contaminant source is less than or equal to the pre-set threshold value when the received user command is the command for performing the perfuming of the clothing C.

Here, the performing the perfuming may include performing drying and perfuming of the clothing C by using hot air after the deodorization is stopped.

Specifically, the performing the perfuming may include supplying hot air into the clothing management device 100 along the first flow path and supplying at least a portion of the hot air which moves along the first flow path into the clothing management device 100 through the second flow path at which the aroma is disposed by adjusting the valve connected to the first flow path.

The performing the perfuming may include supplying hot air into the clothing management device 100 along the plurality of flow paths, and the aroma may be disposed in at least one from among the plurality of flow paths.

Further, the control method of the disclosure may further include stopping perfuming based on determining that the target value has been reached according to the concentration of the aroma in the clothing management device 100 which is detected by the sensor 110 increasing.

In another embodiment, based on the received user command being the command for not performing the perfuming of the clothing C, deodorization may be performed until the concentration of the contaminant source which is detected by the sensor 110 reaches the target value which is lower than the pre-set threshold value.

The sensor 110 may include the first gas sensor 111 and the second gas sensor 113. Here, the control method may further include detecting the concentration of the contaminant source through the first gas sensor 111 which is disposed around the location the clothing C is contained in the clothing management device 100 and detecting the concentration of the aroma through the second gas sensor 113 which is disposed around the location the aroma is sprayed.

The various embodiments of the disclosure may be implemented with software including instructions stored in a machine-readable storage media (e.g., computer). The machine may call an instruction stored in the storage medium, and as a device capable of operating according to the called instruction, may include an electronic device (e.g., the clothing management device 100) according to the above-mentioned embodiment. Based on the instruction being executed by the processor, the processor may directly or using other elements under the control of the processor perform a function corresponding to the instruction. The instruction may include a code generated by a compiler or executed by an interpreter. The machine-readable storage medium may be provided in the form of a non-transitory storage medium. Herein, 'non-transitory' merely means that the storage medium is tangible and does not include a signal, and does not differentiate data being semi-permanently stored or being temporarily stored in the storage medium.

The method according to the various embodiments may be provided included a computer program product. The computer program product may be exchanged between a seller and a purchaser as a commodity. The computer program product may be distributed in the form of a machine-readable storage medium (e.g., a compact disc read only memory (CD-ROM)), or distributed online through an application store (e.g., PLAYSTORE™). In the case of online distribution, at least a portion of the computer program product may be at least stored temporarily in a storage medium such as a server of a manufacturer, a server of an application store, or a memory of a relay server, or temporarily generated.

Each of the elements (e.g., a module or a program) according to various embodiments may be comprised as a single entity or a plurality of entities, and some sub-elements from among the abovementioned sub-elements may be omitted, or different sub-elements may be further included in the various embodiments. Alternatively or additionally, some elements (e.g., modules or programs) may be integrated into one entity to perform the same or similar functions performed by the respective elements prior to integration. Operations performed by a module, a program, or another element, in accordance with various embodiments, may be performed sequentially, in a parallel, repetitively, or in a heuristic manner, or at least some operations may be executed in a different order, omitted or a different operation may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A clothing management device, comprising:
   a sensor;
   a spraying device configured to remove a contaminant source of a clothing contained in the clothing management device;
   an aroma spray device configured to spray an aroma on the clothing; and
   a processor configured to:
      based on a user command being received for managing the clothing, control the spraying device to perform deodorization of the clothing by removing the contaminant source, and
      when the received user command comprises a command to perform perfuming, based on determining that a concentration of the contaminant source detected by the sensor is less than or equal to a pre-set threshold value, control the spraying device to stop the performing of the deodorization of the clothing and control the aroma spray device to perform perfuming of the clothing by using the aroma,
      when the received user command comprises a command for not performing the perfuming, control the spraying device to perform the deodorization of the clothing until the concentration of the contaminant source detected by the sensor reaches a target value lower than the pre-set threshold value,
   wherein the sensor is configured to detect a level of a plurality of different types of contaminant sources,
   wherein the determining that the concentration of the contaminant source detected by the sensor is less than or equal to the pre-set threshold value includes comparing an average in concentration of each of the plurality of different types of the contaminant sources individually against the pre-set threshold value,
   wherein the controlling of the aroma spray device to perform the perfuming of the clothing by using the aroma includes converting the aroma in a liquid state to particles of a fine size by vibrating the aroma using ultrasonic waves, and
   wherein an amount of deodorization performed comprises a first level when the user command comprises the command for not performing perfuming and the amount of deodorization performed comprises a second level when the user command comprises a command for performing perfuming, the first level being greater than the second level.

2. The clothing management device of claim 1, wherein the processor is further configured to, based on determining that a target value is reached according to an increase in a concentration of aroma in the clothing management device detected by the sensor, control the aroma spray device to stop the performing of the perfuming of the clothing.

3. The clothing management device of claim 2,
   wherein the spraying device is further configured to remove the contaminant source of the clothing by spraying steam toward the clothing, and
   wherein the aroma spray device is further configured to perform drying and the perfuming of the clothing by using hot air after the performing of the deodorization stops.

4. The clothing management device of claim 3, wherein the processor is further configured to:
   control the aroma spray device to supply the hot air into the clothing management device along a first flow path, and
   supply at least a portion of the hot air moving along the first flow path into the clothing management device through a second flow path by adjusting a valve connected to the first flow path, the aroma being disposed in the second flow path.

5. The clothing management device of claim 3,
   wherein the processor is further configured to control the aroma spray device to supply the hot air into the clothing management device along a plurality of flow paths, and
   wherein the aroma is disposed in at least one flow path among the plurality of flow paths.

6. The clothing management device of claim 1,
   wherein the sensor comprises a first gas sensor and a second gas sensor, and
   wherein the processor is further configured to:
      detect the concentration of the contaminant source by using the first gas sensor, the first gas sensor being disposed around a location at which the clothing is contained in the clothing management device, and
      detect a concentration of the aroma by using the second gas sensor, the second gas sensor being disposed around a location at which the aroma is sprayed from the aroma spray device.

7. A method of controlling a clothing management device, the method comprising:
   based on a user command being received for managing a clothing contained in the clothing management device, performing deodorization of the clothing for removing a contaminant source of the clothing, the deodorization performed using a spraying device; and
   when the received user command comprises a command to perform perfuming, based on determining that a concentration of the contaminant source detected by a sensor is less than or equal to a pre-set threshold value, stopping the performing of the deodorization of the clothing and performing perfuming of the clothing by using an aroma, the perfuming performed using an aroma spray device,
   when the received user command comprises a command for not performing the perfuming, control the spraying device to perform the deodorization of the clothing until the concentration of the contaminant source detected by the sensor reaches a target value lower than the pre-set threshold value,
   wherein the sensor is configured to detect a level of a plurality of different types of contaminant sources,
   wherein the determining that the concentration of the contaminant source detected by the sensor is less than or equal to the pre-set threshold value includes comparing an average in concentration of each of the plurality of different types of the contaminant sources individually against the pre-set threshold value,
   wherein the performing of perfuming of the clothing by using the aroma includes converting the aroma in a liquid state to particles of a fine size by vibrating the aroma using ultrasonic waves, and wherein an amount of deodorization performed comprises a first level when the user command comprises the command for not performing perfuming and the amount of deodorization performed comprises a second level when the user command comprises a command for performing perfuming, the first level being greater than the second level.

8. The method of claim 7, further comprising:
based on determining that a target value is reached according to an increase in a concentration of an aroma in the clothing management device detected by the sensor, stopping the performing of the perfuming of the clothing.

9. The method of claim 8,
wherein the performing of the deodorization comprises removing the contaminant source of the clothing by spraying steam toward the clothing, and
wherein the performing of the perfuming comprises performing drying and perfuming of the clothing by using hot air after the performing of the deodorization stops.

10. The method of claim 9, wherein the performing of the perfuming of the clothing comprises:
supplying the hot air into the clothing management device along a first flow path; and
supplying at least a portion of the hot air moving along the first flow path through a second flow path by adjusting a valve connected to the first flow path, the aroma being disposed in the second flow path.

11. The method of claim 9,
wherein the performing of the perfuming comprises supplying the hot air into the clothing management device along a plurality of flow paths, and
wherein the aroma is disposed in at least one flow path among the plurality of flow paths.

12. The method of claim 7,
wherein the sensor comprises a first gas sensor and a second gas sensor, and
wherein the method further comprises:
detecting the concentration of the contaminant source by using the first gas sensor, the first gas sensor being disposed around a location at which the clothing is contained in the clothing management device; and
detecting a concentration of the aroma through the second gas sensor, the second gas sensor being disposed around a location at which the aroma is sprayed.

13. The clothing management device of claim 1,
wherein the sensor comprises at least one of an electrochemical sensor, a semiconductor sensor, and a photoionization sensor.

14. The clothing management device of claim 3, wherein the processor is further configured to:
control the spraying device to remove the contaminant source of the clothing by spraying steam toward the clothing using a first flow path,
control the aroma spray device to supply the hot air into the clothing management device along a second flow path, and
supply at least a portion of hot air into the clothing management device through a third flow path, the aroma being disposed in the third flow path,
wherein the first flow path and the second flow path comprise flow paths in which aroma is not disposed.

15. The clothing management device of claim 1, further comprising:
a compressor,
wherein the spraying device is configured to remove the contaminant source by spraying steam together with high-pressure air from the compressor toward the clothing.

* * * * *